(12) United States Patent
van de Goor et al.

(10) Patent No.: US 6,489,774 B1
(45) Date of Patent: Dec. 3, 2002

(54) MINIATURIZED DEVICE FOR ION ANALYSIS, AND METHODS OF USE THEREOF

(75) Inventors: Tom A van de Goor, San Mateo, CA (US); Patrick Kaltenbach, Bischweier (DE)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/349,862

(22) Filed: Jul. 8, 1999

(51) Int. Cl.$^7$ .............................................. G01N 27/02
(52) U.S. Cl. ........................ 324/439; 324/441; 324/443
(58) Field of Search ................................ 324/439, 441, 324/443

(56) References Cited

U.S. PATENT DOCUMENTS

| | | | | |
|---|---|---|---|---|
| 4,577,109 A | * | 3/1986 | Hirschfeld | 250/461.1 |
| 4,785,814 A | * | 11/1988 | Kane | 600/327 |
| 4,842,783 A | * | 6/1989 | Blaylock | 264/1.27 |
| 5,291,226 A | * | 3/1994 | Schantz et al. | 374/124 |
| 5,303,015 A | * | 4/1994 | Schantz et al. | 347/47 |
| 5,500,071 A | | 3/1996 | Kaltenbach | |
| 5,571,410 A | | 11/1996 | Swedberg | |
| 6,033,628 A | | 3/2000 | Kaltenbach | |

OTHER PUBLICATIONS

Gas et al., "High–Frequency Contactless Conductivity Detection in Isotachophoresis," *Journal of Chromatography* 192:253–257 (1980).
Heiger and Weinberger, "Determination of Small Ions by Capillary Zone Electrophoresis With Indirect Photometric Detection," Hewlett–Packard Publication No:12–5963–1138E 1–16 (1994).
Vacik et al., "Improvement of the Performance of a High–Frequency Contactless Conductivity Detector for Isotachophoresis," *Chrom.* 17(322):234–240 (1985).
Zemann et al., "Contactless Conductivity Detection of Capillary Electrophoresis," *Anal. Chem.* 70:563–567 (1998).

* cited by examiner

Primary Examiner—Michael Sherry
Assistant Examiner—Jermele Hollington

(57) ABSTRACT

A miniaturized ion analysis system with a contactless conductivity detection means is described for use in liquid phase sample analysis and detection. The device is formed by microfabrication of microstructures in novel support substrates. The detection means can be fabricated directly in the support body at the point of detection or other locations on the device or, alternatively, may be formed as part of a modular structure that is insertable into the device at the point of detection. In addition, a method is provided for analyzing ionic species present in a sample using the miniaturized ion analysis device. The invention herein is used for the analysis of ionic solutes in the liquid phase.

6 Claims, 20 Drawing Sheets

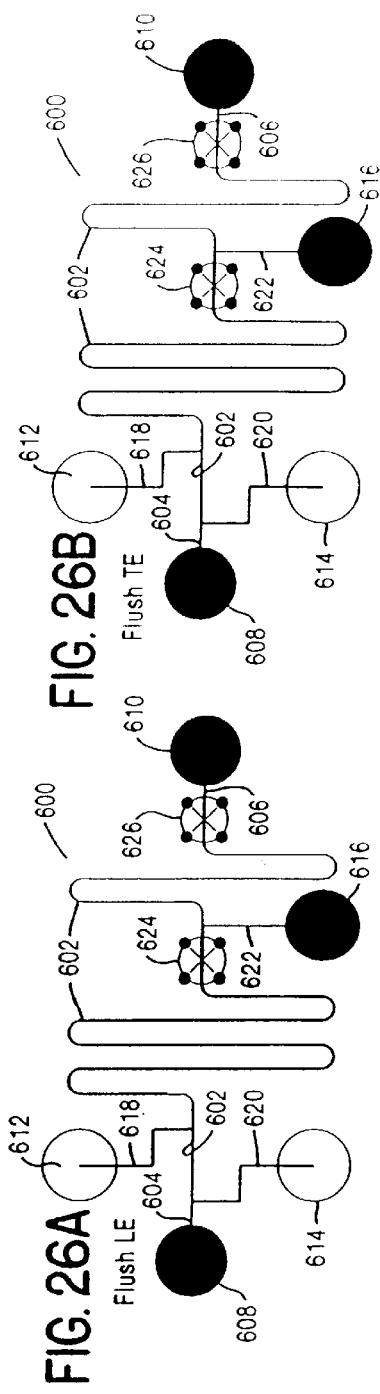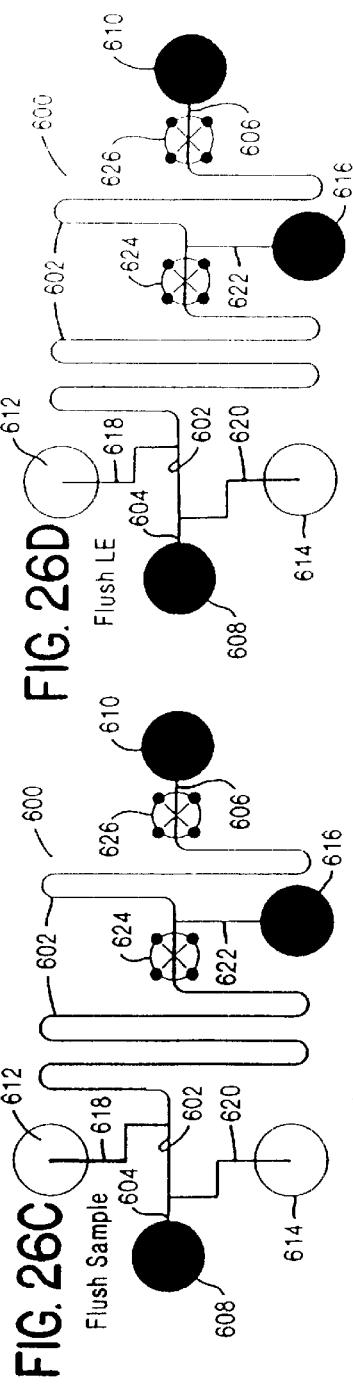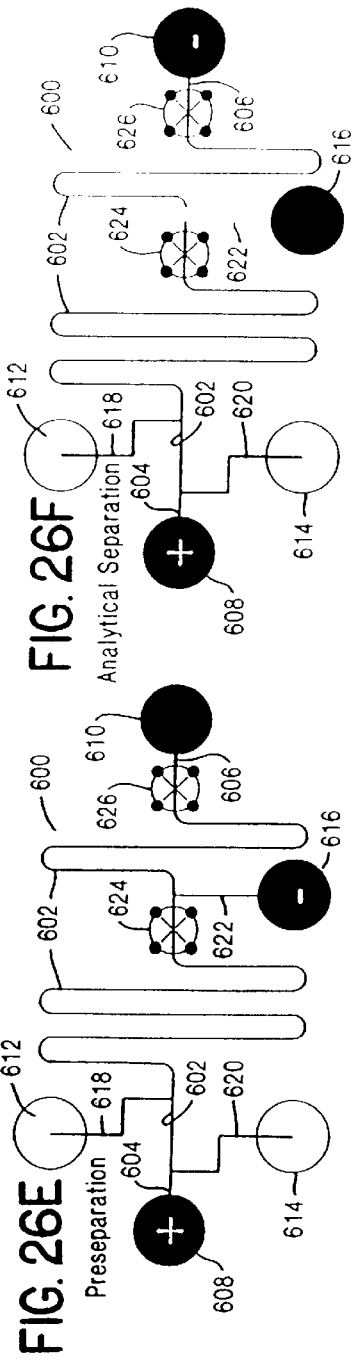

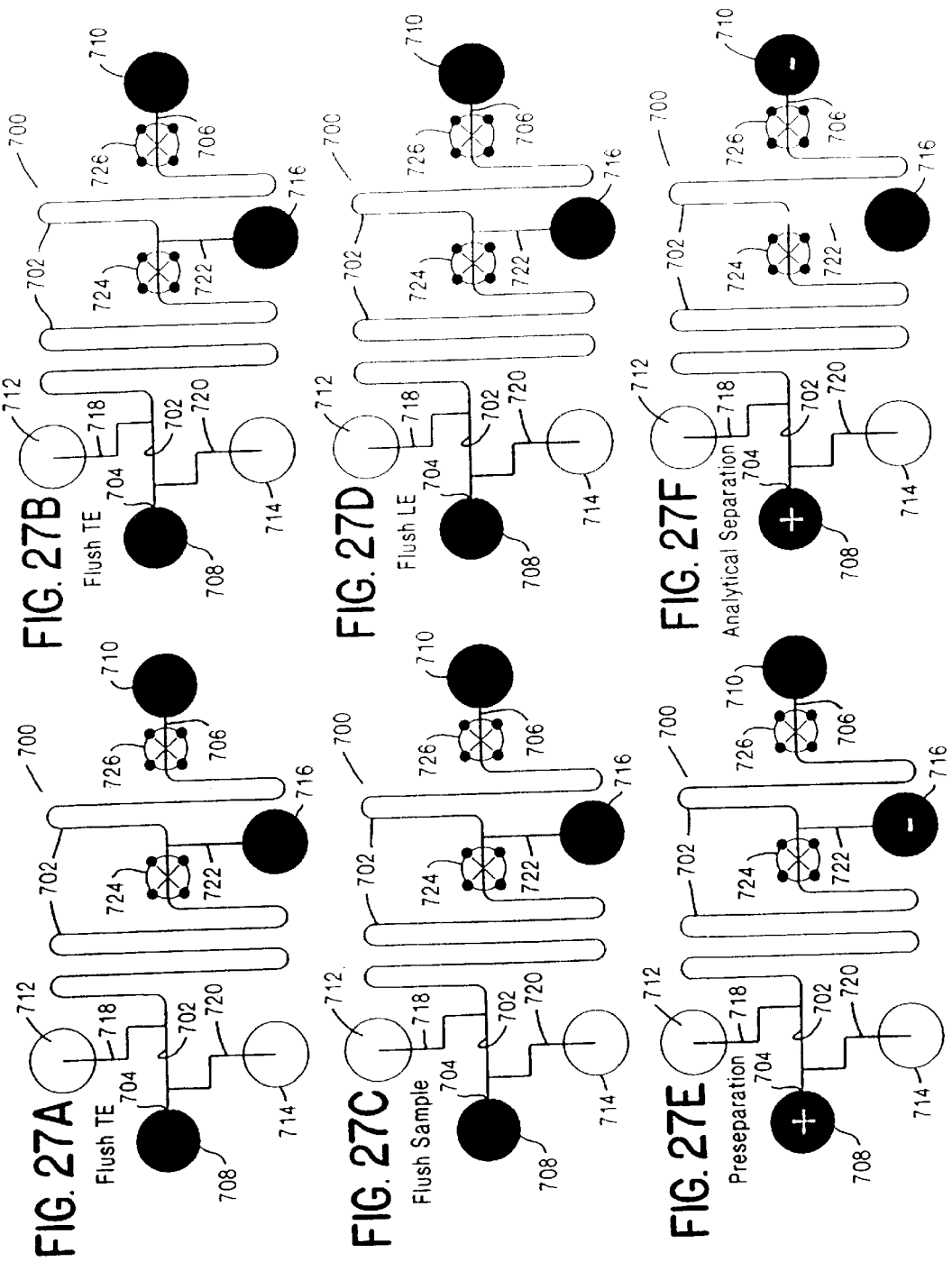

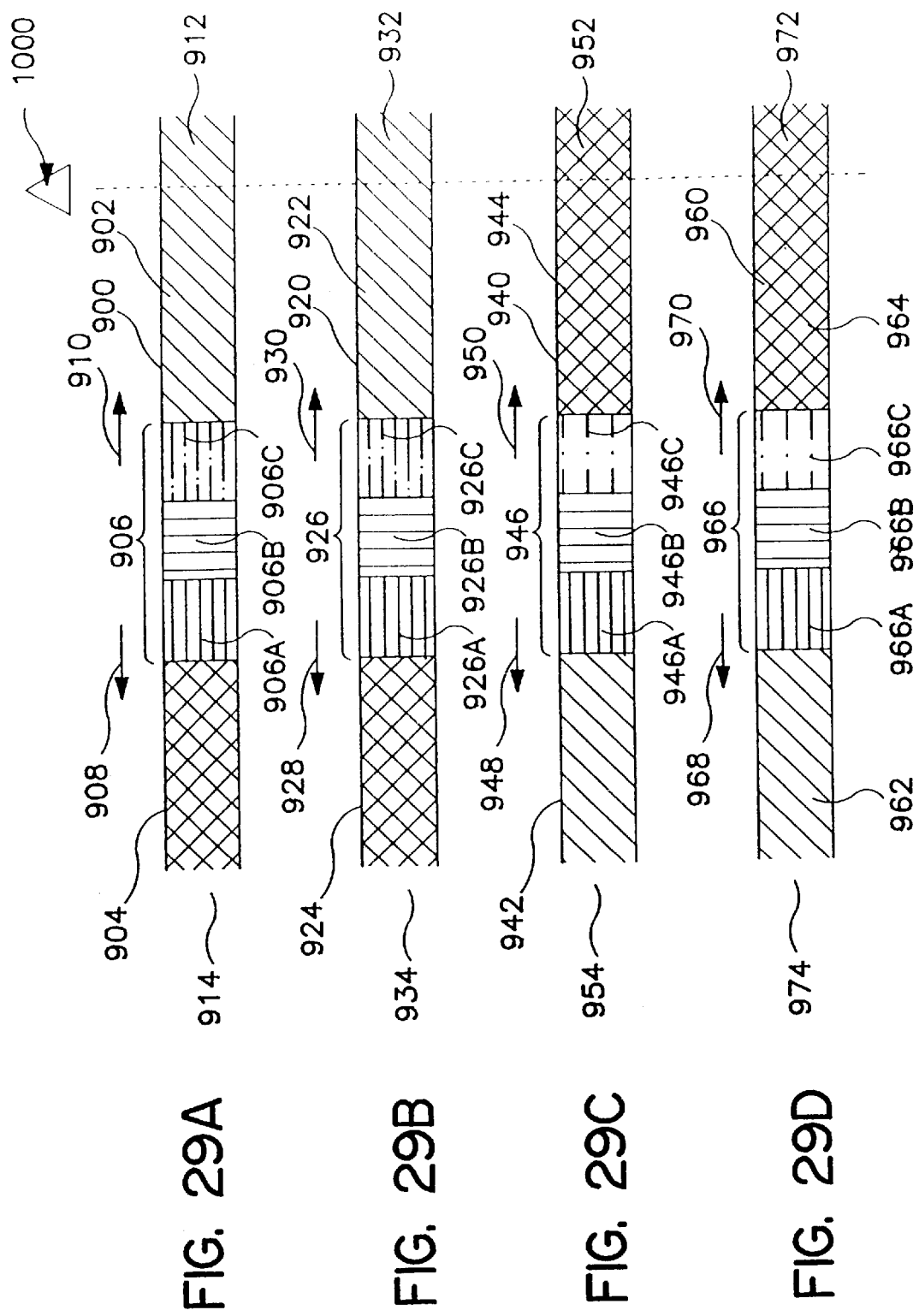

MINIATURIZED DEVICE FOR ION ANALYSIS, AND METHODS OF USE THEREOF

TECHNICAL FIELD

The present invention relates generally to miniaturized liquid phase sample processing and analysis. More particularly, the invention relates to a miniaturized planar sample preparation and analysis device with an on-chip miniature electrophoresis ion analyzer and conductivity detection means. The device, including both ion analyzer and detection means are manufactured using a variety of means suitable for microfabrication of substrate materials such as, but not limited to ablation, molding and embossing.

BACKGROUND

Ion analysis is used in a wide variety of applications, including environmental applications such as water and soil analysis, food industry applications such as wine and beer analysis and in the nuclear power industry.

Currently, there are two main techniques that are used for ion analysis. The more dominant technique is ion chromatography ("IC") in combination with conductivity detection. In this technique, ion exchange columns are used to separate the components of a sample and conductivity measurements are used for detection since may of the ions of interest do not have properties suitable for optical detection. The advantage of IC is that a large quantity of sample can be applied to the column so that a detectable amount of any trace compounds is available for analysis. However, in IC there are problems with the stability of the detection systems and with the reproducibility of ion analysis. In addition, some ions are not easily separated using IC. An additional disadvantage of ion chromatography is the cost per analysis. IC uses expensive instrumentation, expensive columns and solvents and requires generally more sample handling.

More recently, capillary electrophoresis ("CE") has been used for the same applications as ion chromatography. One advantage of CE is that it separates components of a sample based on a different principle and thus is a suitable complementary technique. However, indirect UV detection is typically used in combination with CE to detect ion analytes, which does not have the sensitivity to detect trace sample components. In addition, the ability to load quantities of sample onto a CE apparatus is limited which makes CE less preferred for analysis of trace components of a sample.

Another technique that has been used for ion analysis is isotachophoresis ("ITP"). ITP is performed by sandwiching a sample between a leading and a terminating buffer in a column or capillary and applying an electric field across the leading and terminating buffer reservoirs. The leading buffer is chosen to contain an anion or cation of greater mobility than the anions or cations, respectively, present in the sample. The terminating buffer is selected to contains ions of lesser mobility than those present in the sample. Upon application of an electric field, "sample stacking," i.e., the arrangement in distinct bands of sample substances in order of decreasing mobility, occurs based on the choice of electrolytes. Sample stacking makes it possible to detect trace amounts of a component in a sample. The length of the band for a particular component of the sample depends not on the concentration of the component but on its quantity.

Once separation is complete, all buffer and solute ions migrate at the same velocity. The separation velocity ($v_{ISO}$), which is the same for all zones, is given by $v_{ISO} = \mu_L E_L = \mu_S E_S = \mu_T E_T$, in which $\mu$ is the mobility, E is the electric field strength and subscripts 1, s and t related to leading ion, sample ion and terminating ion. A different electric field develops in each zone because different ions have different mobilities. The highest electric field appears where the lowest mobility ions are present, i.e., the terminating buffer.

The concentration of a solute in its isotachophoretic zone is determined by the composition and concentration of the leading electrolyte. The concentration of the solute is given by $C_A = C_L[\mu_A/(\mu_A+\mu_C)][(\mu_L+\mu_C)/\mu_L]$. Since the mobility of each ion is constant under the defined conditions, the above equation can be written as $C_A = C_L \times k$, in which k is a constant. Thus, the sample ion concentration is directly proportional to the leading ion concentration.

The boundary layer between two isotachophoretic zones is self-sharpening, leading to very high resolution. This self-sharpening effect is derived from the different field strengths in the various zones. For example, if an ion of type A diffuses into the trailing zone of ion of type B, it would be in an environment of lower electric field strength than its own zone. The type A ion's velocity would be decreased from the value $v=\mu_A E_A$ to the value $v=\mu_A E_B$, so it would be retarded relative to the A/B zone boundary. Similarly, if ion B diffuses into the A zone, the field strength is higher, so its velocity would be increased until it is overtake by the A/B zone boundary.

Because each component zone and each of buffer zones have different field strengths, electroosmotic flow in each region will be different region. If electroosmotic flow counter to ITP flow is so high that ITP flow is significantly impeded, the analytes will not separate as desired. To overcome this problem, the viscosity of the buffers could be increased. An alternate solution to the problem that has been used has been to place a membrane designed to stop bulk flow at each end of the ITP column or capillary.

In one technique known as column-coupling ITP, a pre-separation step is used to allow large-volume injection and sample enrichment followed by analytical separation and detection. A commonly used mode of detection in ITP is conductivity detection. Conductivity detection is not only a very sensitive means by which to detect ionic sample components it also provides information on the type of ion detected. However, disadvantages of using conductivity detection concerns the stability of the electrodes that are placed in contact with the liquid buffers and samples. In addition, analysis by ITP involves a complex buffer selection procedure and an understanding of method development for a particular sample.

Silicon micro-machining has been useful in the fabrication of miniaturized liquid phase analysis systems and improvements have been made to overcome the inherent shortcomings of this technique. For example, U.S. Pat. No. 5,500,071 to Kaltenback et al., U.S. Pat. No. RE 36,350 to Swedberg et al. and U.S. Pat. No. 6,033,628 to Kaltenback et al., disclose the use of laser ablation to form microstructures in novel polymer substrates. This permits an enhance symmetry and alignment of structures formed by component parts, enhanced separation capabilities, avoidance of problems with $SiO_2$ chemistry, low-cost manufacturing, the formation of microstructures of any size and geometry, and the incorporation of a detection means for on-column analysis.

SUMMARY OF THE INVENTION

Accordingly, it is a primary object of the invention to provide a novel miniaturized ion analysis device.

It is yet another object of the invention to provide a method for analyzing ionic species present in a sample using the miniaturized ion analysis device.

Additional objects, advantages and novel features of the invention will be set forth in part in the description which follows, and in part will become apparent to those skilled in the art upon examination of the following, or may be learned by practice of the invention.

The present invention is directed to a novel miniaturized ion analysis system for liquid phase isotachophoretic sample analysis and detection. The system comprises contactless conductivity detection ("CCD") means capable of detecting ionic species fluid sample.

In one embodiment of the invention, miniaturized ion analysis system for isotachophoretic sample preparation and analysis is provided. The system comprises:

a microfabricated support body having first and second substantially planar opposing surfaces wherein the support body has a microchannel microfabricated in the first planar surface;

a cover plate arranged over the first planar surface, wherein the cover plate in combination with the first microchannel forms a sample flow compartment;

an inlet port and an outlet port communicating with the sample flow compartment, wherein the inlet and outlet ports enable downstream passage of fluid from an external source through the sample flow compartment; and a contactless conductivity detection means in electrical communication with the sample flow compartment such that the detection means is capable of detecting the presence in the sample flow compartment of a fluid containing a detectable ionic species.

In another embodiment of the invention, a miniaturized ion analysis system for isotachophoretic sample preparation and analysis is provided. The system comprises:

a microfabricated support body having first and second component halves each having substantially planar opposing interior and exterior surfaces;

a first microchannel microfabricated in the interior surface of the first support body half and a second microchannel microfabricated in the interior surface of the second support body half, wherein each of the microchannels is so arranged as to provide the mirror image of the other;

an elongate bore formed by aligning the interior surfaces of the support body halves in facing abutment with each other whereby the microchannels define a sample flow compartment;

an inlet port and an outlet port communicating with the sample flow compartment, the ports enabling the downstream passage of fluid from an external source through the sample flow compartment; and a contactless conductivity detection means situated in electrical contact with the sample flow compartment such that the detection means is capable of detecting the presence in the sample flow compartment of a fluid containing a detectable ionic species.

In yet another embodiment of the invention, a method for analyzing ionic species present in a sample is provided. The method comprises:

providing a miniaturized ion analysis system as disclosed herein;

flushing the sample flow compartment with leading electrolyte;

introducing a sample into the sample flow compartment such that the sample is in fluidic and ionic communication with the leading electrolyte;

introducing terminating electrolyte into the sample flow compartment such that the sample is in fluidic and ionic communication with the leading electrolyte;

stacking the ionic species present in the sample by applying a current across the leading and terminating electrolytes to provide stacked ionic species; and detecting the presence in the sample flow compartment of the stacked ionic species.

A particular advantage of the present invention is the use of processes other than silicon micromachining techniques or etching techniques to create miniaturized columns in a wide variety of polymeric, ceramic, glass, composite substrates having desirable attributes for an analysis portion of a separation system. More specifically, it is contemplated herein to provide a miniaturized ion analysis system prepared by ablating, molding or embossing component microstructures in a substrate using techniques well known in the art. In one preferred embodiment, a miniaturized ion analysis system is formed by providing two substantially planar halves having microstructures microfabricated thereon, which, when the two halves are folded upon each other, define a sample flow compartment featuring enhanced symmetry and axial alignment.

Use of microfabrication techniques, e.g., laser ablation, to form a miniaturized ion analysis system according to the present invention affords several advantages over prior etching and micromachining techniques used to form systems in silicon or silicon dioxide materials. Initially, the capability of applying rigid computerized control over such processes allows microstructure formation to be executed with great precision, thereby enabling a heightened degree of alignment in structures formed by component parts. For example, laser ablation processes avoid problems encountered with microlithographic isotropic etching techniques which may undercut masking during etching, giving rise to asymmetrical structures having curved side walls and flat bottoms.

Microfabrication, in particular, laser ablation, enables the production of microstructures with greatly reduced component size. In this regard, microstructures formed as described herein are capable of having aspect ratios several orders of magnitude higher than possible using prior etching techniques, thereby providing enhanced sample processing capabilities in such devices. For example, the use of laser-ablation processes to form microstructures in substrates such as polymers increases ease of fabrication and lowers per-unit manufacturing costs in the subject devices as compared to prior approaches such as micromachining devices in silicon. In this regard, devices formed according to the invention in low-cost substrates have the added feature of being capable of use as substantially disposable miniaturized analysis units.

Laser ablation or other microfabrication techniques used in a planar substrate allows for formation of microstructures of almost any geometry or shape. This feature not only enables the formation of complex device configurations, but further allows for integration of sample injection, sample preparation, pre- or post-separation chemical modification and a variety of detection means, in particular, a CCD means, in a miniaturized ion analysis system.

By the present invention, inherent weaknesses existing in prior approaches to liquid phase analysis device miniaturization, and problems in using silicon micromachining techniques to form miniaturized analysis devices have been addressed. Accordingly, the present invention discloses a miniaturized ion analysis system capable of liquid phase isotachophoretic sample preparation and analysis on a wide array of liquid samples.

BRIEF DESCRIPTION OF THE DRAWINGS

In the course of this description, reference will be made to the attached drawings, wherein like parts denote like parts throughout and wherein:

FIGS. 26A–26F is a schematic diagram of one mode of operation of a miniaturized ion analysis system using a CCD means for ion analysis of a sample in a sample processing compartment using isotachophoresis. In this embodiment, both sample preparation and analytical separation stages are conducted in ITP mode. In this figure, the red line represents leading electrolyte, the blue line represents terminating electrolyte and the yellow line represents sample.

FIGS. 27A–27F is a schematic diagram of one mode of operation of a miniaturized ion analysis system using a CCD means for ion analysis of a sample in a sample processing compartment using isotachophoresis and capillary zone electrophoresis. In this embodiment, sample preparation is conducted in ITP mode and analytical separation is conducted in CZE mode. In this figure, the red line represents leading electrolyte, the blue line represents terminating electrolyte and the yellow line represents sample.

FIG. 29 is a schematic illustration of the four modes in ITP experiments with electroosmotic flow. FIG. 29A is an illustration of the cationic mode, FIG. 29B is the anionic mode, FIG. 29C is the reversed cationic mode and FIG. 29D is the reversed anionic mode.

DETAILED DESCRIPTION OF THE INVENTION

Figure 1:
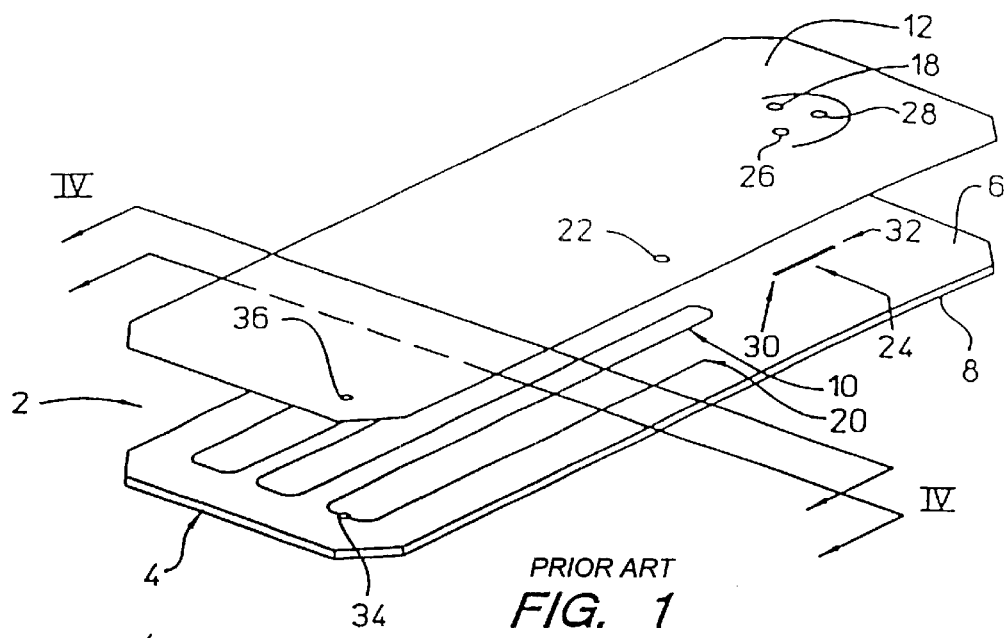
FIG. 1 is an exploded view of a prior art miniaturized column device constructed in accordance with the present invention.

Before the invention is described in detail, it is to be understood that this invention is not limited to the particular component parts of the devices described or process steps of the methods described as such devices and methods may vary. It is also to be understood that the terminology used herein is for purposes of describing particular embodiments only, and is not intended to be limiting. It must be noted that, as used in the specification and the appended claims, the singular forms "a," "an" and "the" include plural referents unless the context clearly dictates otherwise. Thus, for example, reference to "an analyte" includes mixtures of analytes, reference to "a detection means" includes two or more such detection means, reference to "a sample processing compartment" includes more than one such compartment, reference to "contactless conductivity detection means" includes more than one such detection means, and the like.

In this specification and in the claims that follow, reference will be made to a number of terms which shall be defined to have the following meanings:

The term "substrate" and "support body" are used interchangeably herein to refer to any material which can be microfabricated, e.g., ablated, molded or embossed, to have desired miniaturized surface features. The substrate can be a polymer, a ceramic, a glass, a metal, a composite thereof, a laminate thereof, or the like. A "composite" is a composition comprised of unlike materials. The composite may be a block composite, e.g., an A-B-A block composite, an A-B-C block composite, or the like. Alternatively, the composite may be a heterogeneous, i.e., in which the materials are distinct or in separate phases, or homogeneous combination of unlike materials. As used herein, the term "composite" is used to include a "laminate" composite. A "laminate" refers to a composite material formed from several different bonded layers of same or different materials.

Accordingly, in one embodiment, a miniaturized ion analysis device is formed herein using suitable substrates, such as laser ablatable polymers (including polyimides and the like) and ceramics (including aluminum oxides and the like), as well as glass and substrates. Further, a miniaturized ion analysis device can be formed using a composite substrate. One particularly preferred composite substrate comprises a polyimide laminate formed from a first layer of polyimide, such as Kapton® (DuPont; Wilmington, Del.), that has been co-extruded with a second, thin layer of a thermal adhesive form of polyimide known as KJ(® (DuPont). This thermoplastic adhesive can be applied to one or both sides of the first polyimide layer, thereby providing a means for producing a laminate of desired thickness. Other preferred composite substrates include a polymer-metal laminates, e.g., polyimide coated with copper, a ceramic-in-metal or a polymer-in-metal composite. Metal-coated ceramics and other metal-coated polymers may well be used in which the metal-coated side thereof can be used for patterning of the electrode structures while the polymer side can be used for patterning the fluid channels.

The term "sample processing compartment" is used herein to refer to a region of the support in which sample handling is carried out. Sample handling includes the entire range of operations capable of being performed on the sample from its introduction into the compartment until its removal for use. Thus, sample processing includes operations that effect sample preparation and/or sample separation. Such operations may include but are not limited to: concentration of a sample from a dilute solution; chemical modifications of sample components; chromatographic and/or electrophoretic separation of sample components; removal of interfering molecules and ions; and the like. The sample processing compartment frequently will include one or more access ports for introducing materials into, and withdrawing materials from the compartment (e.g., sample, fluids and reagents).

The term "sample flow channel" is used herein to refer to the flow path extending from the first end of the sample processing compartment of the miniaturized separation device to the second end thereof. A "sample flow channel" can be a flow path that extends from, for example, an on-device fluid reservoir to another sample flow channel or from one sample flow channel to another sample flow channel. In addition, a sample flow channel can extend from a sample-introduction access port sample to a sample-withdrawal access port.

The term "sample handling region" refers to a portion of a microchannel, or to a portion of a "sample processing compartment" that is formed upon enclosure of the microchannel by a cover plate or substrate in which a mirror image of the microchannel has been microfabricated as described below, that includes a "sample flow component" or a "sample treatment component." By the term "sample flow component" is intended a portion of the sample processing compartment that interconnects sample treatment components.

A "sample treatment component" is a portion of the sample processing compartment in which particular sample preparation chemistries are done. In particular, an analyte of interest is generally obtained in a matrix containing other species which may potentially interfere with the detection and analysis of the analyte. Accordingly, a sample treatment component is a portion of the sample processing compartment in which analyte separation from a matrix is effected. Examples of functions which may be served by the sample treatment component include chromatographic separations, electrophoretic separations, electrochromatographic separations, and the like.

As "detection means" is intended to include any means, structure or configuration that allows the interrogation of a sample within a sample processing compartment or a sample flow channel using analytical detection means well known in the art. Thus, a detection means includes one or more apertures, elongated apertures or grooves that communicate with the sample processing compartment and allow an external detection apparatus or device to be interfaced with the sample processing compartment to detect an analyte passing through the compartment. A detection means need not come into direct contact with the sample in the sample processing department. Thus, for example, a conductivity detection means or photometric detection means can be integrated into the substrate in association with the sample processing compartment such that the detection means does not contact the sample yet provides information about the ionic content of the sample.

Thus, the term "contactless conductivity detector" refers to any means, structure or configuration which allows one to interrogate a sample using electrodes applied to the surface of the substrate that opposes the surface in which the sample processing compartment has been microfabricated. Using such a detector, the electrodes do not come in contact with the sample being detected. By contrast, direct-contact conductivity detectors, in which the electrodes come into direct contact with the sample, suffer from the disadvantage that electrode processes can occur on the sensing electrodes and the reproducibility of the measurements can be relatively poor as a result. Designs of contactless conductivity detectors that can be used in the invention disclosed and claimed herein are described in Gaš et al. (1980) *J. Chromatog.* 192:253–257, Vacík et al. (1985) *Chrom.* 17:233–240, Zemann et al. (1998) *Anal. Chem.* 70:563–567, and Da Silva (1998) *Anal. Chem.* 70:4339–4343.

A "photometric detector" refers to a means for detecting nonchromogenic ionic species by adding a visualizing reagent to the sample. In this technique, a UV-absorbing solute of the same charge as the separands (i.e., a co-ion) serves as an additive to the buffers and sample. This additive elevates the baseline. When solute ions are present, they displace the visualizing reagent as required by the principle of electroneutrality. As the separated ions migrate past a detection window, they are measured as negative peaks relative to the high baseline. See Hewlett-Packard Publication No. 12-5963-1138E.

An "optical detection path" refers to a configuration or arrangement of detection means to form a path whereby radiation, such as a ray of light, is able to travel from an external source to a means for receiving radiation—wherein the radiation traverses the sample processing compartment and can be influenced by the sample or separated analytes in the sample flowing through the sample processing compartment. An optical detection path is generally formed according to the invention by positioning a pair of detection means directly opposite each other relative to the sample processing compartment. In this configuration, analytes passing through the sample processing compartment can be detected via transmission of radiation orthogonal to the major axis of the sample processing compartment (and, accordingly, orthogonal to the direction of electro-osmotic flow in an electrophoretic separation). A variety of external optical detection techniques can be readily interfaced with the sample processing compartment using an optical detection path including, but not limited to, UV/Vis, Near IR, fluorescence, refractive index (RI) and Raman techniques.

As used herein, a "lightguide means" refers to a substantially long, thin thread of a transparent substance which can be used to transmit light. Lightguide means useful in the practice of the invention include optical fibers, integrated lens configurations and the like. In particularly preferred embodiments, optical fibers are interfaced with detection means to enable optical detection techniques known in the art. The terms "optical fiber," "fiber optic waveguide" or "optical fiber means" are used herein to refer to a single optical fiber or a bundle optical fibers, optionally encased in a protective cladding material. Examples of suitable optical fiber substrate materials include glass, plastic, glass/glass composite and glass/plastic composite fibers. A critical characteristic of optical fibers is attenuation of an optical signal. Further, a chemical sensor can be incorporated into a fiber optic waveguide in a manner such that the chemical sensor will interact with the liquid sample analyte. Structures, properties, functions and operational details of such fiber optic chemical sensors can be found in U.S. Pat. No. 4,577,109 to Hirschfeld, U.S. Pat. No. 4,785,814 to Kane, and U.S. Pat. No. 4,842,783 to Blaylock.

The use of microfabrication techniques such as, but not limited to, laser ablation, molding and embossing, in the practice of the invention allows for a high degree of precision in the alignment of micro-scale components and structures, which alignment has either been difficult or not possible in prior substrate-based devices. Thus, the term "microalignment" as used herein refers to the precise and accurate alignment of microfabricated features, including the enhanced alignment of complementary microchannels or microcompartments with each other, inlet and/or outlet ports with microchannels or separation compartments, detection means with microchannels or separation compartments, detection means with other detection means, and the like.

The term "microalignment means" is defined herein to refer to any means for ensuring the precise microalignment of microfabricated features in a miniaturized column device. Microalignment means can be formed in the column devices either by laser ablation or by other methods of fabricating shaped pieces well known in the art. Representative microalignment means that can be employed herein include a plurality of co-axially arranged apertures microfabricated in component parts and/or a plurality of corresponding features in column device substrates, e.g., projections and mating depressions, grooves and mating ridges or the like. Alternative alignment means includes features forms in component parts such as pin and mating aperture. Further, the accurate microalignment of component parts can be effected by forming the miniaturized columns in flexible substrates having at least one fold means microfabricated therein, such that sections of the substrate can be folded to overlie other sections thereby forming composite microscale compartments, aligning features such as apertures or detection means with separation compartments, or forming micro-scale separation compartments from microchannels. Such fold means can be embodied by a row of spaced-apart perforations fabricated in a particular substrate, a contiguous slot-like depression or a series spaced-apart slot-like depressions or apertures microfabricated in the substrate so as to extend only part way therethrough, or the like. The perforations or depressions can have circular, diamond, hexagonal or other shapes that promote hinge formation along a predetermined straight line.

The term "liquid phase analysis" is used to refer to any analysis which is done on either small and/or macromolecular solutes in the liquid phase. Accordingly, "liquid phase analysis" as used herein includes chromatographic separations, electrophoretic separations, and electrochromatographic separations.

In this regard, "chromatographic" processes generally comprise preferential separations of components, and include reverse-phase, hydrophobic interaction, ion exchange, molecular sieve chromatography and like methods. "Electrophoretic" separations refers to the migration of particles or macromolecules having a net electric charge where said migration is influenced by an electric field. Accordingly electrophoretic separations contemplated for use in the invention include separations performed in columns packed with gels (such as poly-acrylamide, agarose and combinations thereof) as well as separations performed in solution.

"Electrochromatographic" separations refer to combinations of electrophoretic and chromatographic techniques.

"Isotachophoresis" as a form of electrophoresis refers to the separation of and detection of ionic species based ion stacking relative to a leading and a trailing electrolyte. See, e.g., Everaerts et al. (1976) *Isotachophoresis, Theory, Instrumentation and Applications* (J. Chromatog. Library, Vol. 6, Elsevier, Amsterdam).

The term "motive force" is used to refer to any means for inducing movement of a sample along a column in a liquid phase analysis, and includes application of an electric potential across any portion of the column, application of a pressure differential across any portion of the column or any combination thereof.

The term "surface treatment" is used to refer to preparation or modification of the surface of a microchannel which will be in contact with a sample during separation, whereby the separation characteristics of the device are altered or otherwise enhanced. Accordingly, "surface treatment" as used herein includes: physical surface adsorptions; covalent bonding of selected moieties to functional groups on the surface of microchannel substrates (such as to amine, hydroxyl or carboxylic acid groups on condensation polymers); methods of coating surfaces, including dynamic deactivation of channel surfaces (such as by adding surfactants to media), polymer grafting to the surface of channel substrates (such as polystyrene or divinyl-benzene), sputter deposition of metallic materials and thin-film deposition of materials such as diamond or sapphire to microchannel substrates.

The term "laser ablation" is used to refer to a machining process using a high-energy photon laser such as an excimer laser to ablate features in a suitable substrate. The excimer laser can be, for example, of the $F_2$, ArF, KrCl, KrF, or XeCl type.

The microstructures in the miniaturized separation device of the invention, e.g., sample processing compartments, injection means, detection means and micro-alignment means, may be formed by microfabrication in a support body such as a polymeric, ceramic, glass, metal or composite substrate. For example, laser ablation techniques can be used with any UV-absorbing material such as a polymer or ceramic material (see U.S. Pat. Nos. 5,500,071 and 5,571,410).

In general, with respect to laser ablation, any substrate that is UV-absorbing provides a suitable substrate for the support body. The support body may comprise a substantially planar substrate such as a polyimide film that is both laser ablatable and flexible so as to enable folding after ablation; however, the particular substrate selected or microfabrication technique is not considered to be limiting in the invention. Accordingly, microstructures of selected configurations can be formed by imaging a lithographic mask onto a suitable substrate, such as a polymer or ceramic material, and then laser ablating the substrate with laser light in areas that are unprotected by the lithographic mask.

In laser ablation, short pulses of intense ultraviolet light are absorbed in a thin surface layer of material within about 1 $\mu$m or less of the surface. Preferred pulse energies are greater than about 100 millijoules per square centimeter and pulse durations are shorter than about 1 microsecond. Under these conditions, the intense UV light photo-dissociates the chemical bonds in the material. Furthermore, the absorbed UV energy is concentrated in such a small volume of material that it rapidly heats the dissociated fragments and ejects them away from the surface of the material. Because these processes occur so quickly, there is no time for heat to propagate to the surrounding material. As a result, the surrounding region is not melted or otherwise damaged, and the perimeter of ablated features can replicate the shape of the incident optical beam with precision on the scale of about one micrometer.

Although laser ablation has been described herein using an excimer laser, it is to be understood that other UV light sources with substantially the same optical wavelength and energy density may be used to accomplish the ablation process. Preferably, the wavelength of such an ultraviolet light source will lie in the 150 nm to 400 nm range to allow high absorption in the substrate to be ablated. Furthermore, the energy density should be greater than about 100 millijoules per square centimeter with a pulse length shorter than about 1 microsecond to achieve rapid ejection of ablated material with essentially no heating of the surrounding remaining material. Laser ablation techniques, such as those described above, have been described in the art. Znotins et al., Laser Focus Electro Optics, (1987) pp. 54–70; U.S. Pat. Nos. 5,291,226 and 5,305,015 to Schantz et al.

A frequency multiplied YAG laser can also be used in place of the excimer laser. In such a case, a complex microstructure pattern useful for practicing the invention can be formed on a suitable polymeric or ceramic substrate by combining a masking process with a laser ablation means, such as in a step-and-repeat process, where such processes would be readily understood by one of ordinary skill in the art.

The term "injection molding" is used to refer to a process for molding plastic or nonplastic ceramic shapes by injecting a measured quantity of a molten plastic or ceramic substrate into dies (or molds). In one embodiment of the present invention, miniaturized column devices may be produced using injection molding.

More particularly, it is contemplated to form a mold or die of a miniaturized ion analysis device wherein excimer laser-ablation or other microfabrication technique is used to define an original microstructure pattern in a suitable polymer substrate. The microstructure thus formed may then be coated by a very thin metal layer and electroplated (such as by galvano forming) with a metal such as nickel to provide a carrier. When the metal carrier is separated from the original polymer, a mold insert (or tooling) is provided having the negative structure of the polymer. Accordingly, multiple replicas of the microstructure pattern may be made in suitable substrates using injection molding techniques well known in the art.

The term "LIGA process" is used to refer to a process for fabricating microstructures having high aspect ratios and increased structural precision using synchrotron radiation lithography, galvanoforming, and plastic molding. In a LIGA process, radiation sensitive plastics are lithographically irradiated at high energy radiation using a synchrotron source to create desired microstructures (such as channels, ports, apertures and micro-alignment means), thereby forming a primary template.

The primary template is then filled with a metal by electrodeposition techniques. The metal structure thus formed comprises a mold insert for the fabrication of secondary plastic templates which take the place of the primary template. In this manner highly accurate replicas of the original microstructures may be formed in a variety of substrates using injection or reactive injection molding techniques. The LIGA process has been described by Becker et al. (1986) *Microelectric Engineering* 4:35–56. Descriptions of numerous polymer substrates which may be injection molded using LIGA templates, and which are suitable substrates in the practice of the subject invention, may be found in Allcock et al. (1981) Contemporary Polymer Chemistry (Prentice-Hall, Inc., New Jersey).

"Optional" or "optionally" means that the subsequently described feature or structure may or may not be present in the integrated planar separation device or that the subsequently described event or circumstance may or may not occur, and that the description includes instances where said feature or structure is present and instances where the feature or structure is absent, or instances where the event or circumstance occurs and instances where it does not. For example, the phrase "an integrated separation device optionally having detection means" intends that access ports may or may not be present on the device and that the description includes both circumstances where access ports are present and absent.

Accordingly, the invention concerns formation of a miniaturized ion analysis device including CCD means using microfabrication techniques in a suitable substrate. It is also contemplated to form ion analysis devices according to the invention using injection molding techniques wherein the original microstructure has been formed by an excimer laser ablation process, a LIGA process, or other suitable microfabrication process.

A preferred substrate for practicing this invention using laser ablation comprises a polyimide material such as those available under the trademarks Kapton® or Upilex® from DuPont (Wilmington, Del.), although the particular substrate selected may comprise any other suitable polymer or ceramic substrate. Polymer materials particularly contemplated herein include materials selected from the following classes: polyimide, polycarbonate, polyester, polyamide, polyether, polyolefin, or mixtures thereof Further, the polymer material selected may be produced in long strips on a reel, and, optional sprocket holes along the sides of the material may be provided to accurately and securely transport the substrate through a step-and-repeat process.

According to the invention, the selected polymer material is transported to a laser processing chamber and laser-ablated in a pattern defined by one or more masks using laser radiation. In a preferred embodiment, such masks define all of the ablated features for an extended area of the material, for example encompassing multiple apertures (including inlet and outlet ports), micro-alignment means and sample processing chambers.

Alternatively, patterns such as the aperture pattern, the sample processing channel pattern, etc., may be placed side by side on a common mask substrate which is substantially larger than the laser beam. Such patterns may then be moved sequentially into the beam. In other contemplated production methods, one or more masks may be used to form apertures through the substrate, and another mask and laser energy level (and/or number of laser shots) may be used to define sample processing channels which are only formed through a portion of the thickness of the substrate. The masking material used in such masks will preferably be highly reflecting at the laser wavelength, consisting of, for example, a multilayer dielectric material or a metal such as aluminum.

The laser ablation system employed in the invention generally includes beam delivery optics, alignment optics, a high precision and high speed mask shuttle system, and a processing chamber including mechanism for handling and positioning the material. In a preferred embodiment, the laser system uses a projection mask configuration wherein a precision lens interposed between the mask and the substrate projects the excimer laser light onto the substrate in the image of the pattern defined on the mask.

It will be readily apparent to one of ordinary skill in the art that microfabrication techniques may be used to form miniaturized sample processing channels and apertures in a wide variety of geometries. For example, any geometry that does not include undercutting may be provided using ablation techniques, such as modulation of laser light intensity across the substrate, stepping the beam across the surface or stepping the fluence and number of pulses applied to each location to control corresponding depth. Further, channels or chambers produced according to the invention are easily fabricated having ratios of channel depth to channel width which are much greater than previously possible using etching techniques such as silicon micromachining. Such aspect ratios can easily exceed unity, and may even reach to 10. Furthermore, the aspect ratio of, e.g., laser-ablated channels and chambers can be less than one, i.e., the width of the channel or chamber can be greater than the depth.

In a preferred embodiment of the invention, channels of a semi-circular cross section are laser ablated by controlling exposure intensity or by making multiple exposures with the beam being reoriented between each exposure. Accordingly, when a corresponding semi-circular channel is aligned with a channel thus formed, a sample processing chamber of highly symmetrical circular cross-section is defined which may be desirable for enhanced fluid flow through the sample processing device.

As a final step in laser ablation processes, a cleaning step is performed wherein the laser-ablated portion of the substrate is positioned under a cleaning station. At the cleaning station, debris from the laser ablation are removed according to standard industry practice.

As will be appreciated by those working in the field of liquid phase analysis devices, the above-described method may be used to produce a wide variety of miniaturized devices. One such device is represented in FIG. 1 where a particular embodiment of a miniaturized column device is generally indicated at 2. Generally, miniaturized column 2 is formed in a selected substrate 4 using laser ablation techniques. The substrate 4 generally comprises first and second substantially planar opposing surfaces indicated at 6 and 8 respectively, and is selected from a material other than silicon which is UV absorbing and, accordingly, laser-ablatable.

In a particular embodiment of the invention, the miniaturized column device 2 comprises a column structure ablated on a chip, which, in the practice of the invention may be a machinable form of the plastic polyimide such as Vespel®. It is particularly contemplated in the invention to use such a polyimide substrate as, based on considerable experience with the shortcomings of fused silica and research into alternatives thereof, polyimides have proved to be a highly desirable substrate material for the analysis portion of a liquid phase sample processing system.

In this regard, it has been demonstrated that polyimides exhibit low sorptive properties towards proteins, which are known to be particularly difficult to analyze in prior silicon dioxide-based separation systems. Successful demonstrations of separations with this difficult class of solutes typically ensures that separation of other classes of solutes will be not be problematic. Further, since polyimide is a condensation polymer, it is possible to chemically bond groups to the surface which may provide a variety of desirable surface properties, depending on the target analysis. Unlike prior silicon dioxide based systems, these bonds to the polymeric substrate demonstrate pH stability in the basic region (pH 9–10).

Figure 2:
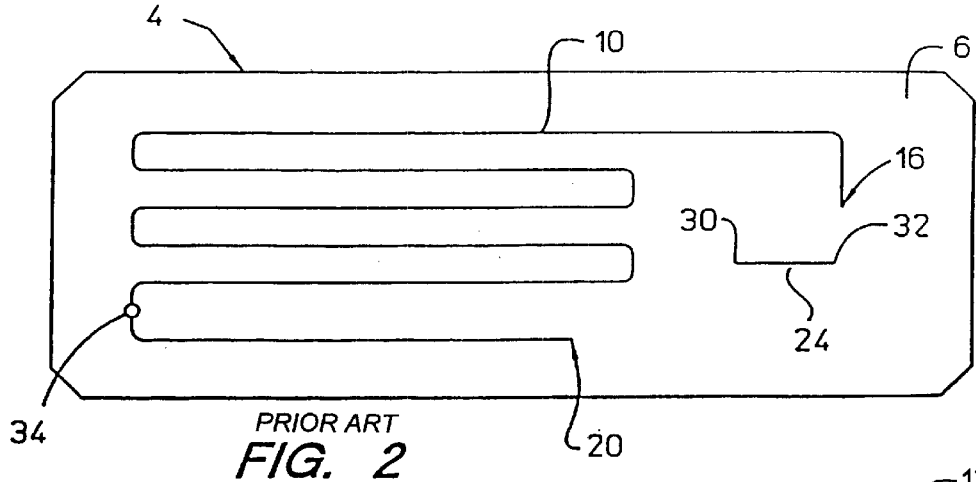
FIG. 2 is a plan view of the interior surface of the prior art miniaturized column device of FIG. 1.
Figure 3:
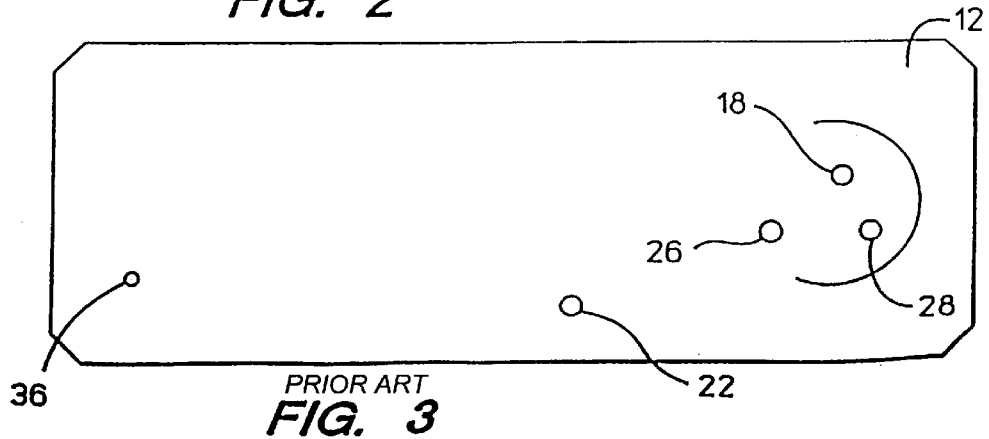
FIG. 3 is a plan view of the exterior surface of the prior art device of FIG. 1.

Referring now to FIGS. 1–3, the substrate 4 has a microchannel 10 laser-ablated in a first planar surface 6. It will be readily appreciated that, although the microchannel 10 has been represented in a generally extended form, microchannels formed according to the invention may be ablated in a large variety of configurations, such as in a straight, serpentine, spiral, or any tortuous path desired. Further, as described in greater detail above, the microchannel 10 may be formed in a wide variety of channel geometries including semi-circular, rectangular, rhomboid, and the like, and the channels may be formed in a wide range of aspect ratios. It is also noted that a device having a plurality of microchannels laser-ablated thereon falls within the spirit of the present invention.

Figure 4:
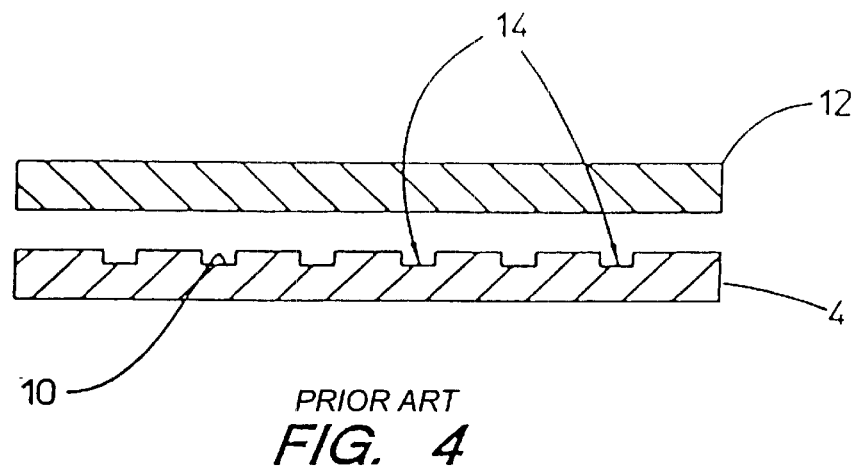
FIG. 4 is a cross-sectional side view of the prior art miniaturized column device of FIG. 1, taken along lines IV—IV and showing formation of a sample processing compartment according to the invention.

Referring particularly to FIGS. 1 and 4, a cover plate 12 is arranged over said first planar surface 6 and, in combination with the laser-ablated microchannel 10, forms an elongate sample processing compartment 14. Cover plate 12 may be formed from any suitable substrate such as polyimide, the selection of the substrate only being limited by avoidance of undesirable separation surfaces such as silicon or silicon dioxide materials.

According to the invention, cover plate 12 may be fixably aligned over the first planar surface 6 to form a liquid-tight sample processing compartment by using pressure sealing techniques, by using external means to urge the pieces together (such as clips, tension springs or associated clamping apparatus) or by using adhesives well known in the art of bonding polymers, ceramics and the like.

Referring to FIGS. 1–4, a particular embodiment of the invention is shown wherein cover plate 12 further comprises apertures ablated therein. In this regard, a first aperture communicates with the sample processing compartment 14 at a first end 16 thereof to form an inlet port 18 enabling the passage of fluid from an external source into said sample processing compartment. A second aperture communicates with the sample processing compartment 14 at a second end 20 thereof to form an outlet port 22 enabling passage of fluid from the sample processing compartment to an external receptacle. Accordingly, a miniaturized column device is formed having a flow path extending from the first end 16 of the sample processing compartment and passing to the second end 20 thereof, whereby liquid phase analysis of samples may be carried out using techniques well known in the art.

Referring still to FIGS. 1–4, a particular embodiment of the invention is shown comprising sample introduction means laser-ablated into both the substrate 4 and cover plate 12. An internally ablated by-pass channel 24 is formed in substrate 4, said channel 24 being disposed near the first end 16 of the sample processing compartment. Two additional apertures 26 and 28 are formed in cover plate 12 and are arranged to cooperate with first and second ends (indicated at 30 and 32 respectively) of the by-pass channel 24. In this manner, a sample being held in an external reservoir may be introduced into by-pass channel 24 to form a sample plug of a known volume (defined by the dimensions of the channel 24). The sample plug thus formed may then be introduced into the first end 16 of the sample processing compartment 14 via inlet port 18 by communicating external mechanical valving with said inlet port and laser-ablated apertures 26 and 28 and flushing solution through the by-pass channel 24 into the sample processing compartment.

It is noted that the ablated by-pass channel 24 and apertures 26 and 28 further enable a wide variety of sample introduction techniques to be practiced according to the invention. Particularly, having a by-pass channel which is not connected to the sample processing compartment allows a user to flush a sample through the by-pass channel without experiencing sample carry-over or column contamination. As will be appreciated by one of ordinary skill in the art after reading this specification, one such sample introduction technique may be effected by butt-coupling an associated rotor to a stator (not shown) on the external surface of a miniaturized column where the rotor selectively interfaces external tubing and fluid sources with inlet port 18 and apertures 26 and 28, allowing a sample to be flushed from the by-pass channel 24 into external tubing from which the sample may then be introduced into the column via inlet port 18 for liquid phase analysis thereof. In this regard, a miniaturized column device formed in a polyimide substrate enables a ceramic rotor, pressed to the device using tensioned force (to form a liquid-tight seal), to still rotate between selected aperture positions on the device due to the friction characteristics of the two materials. Other suitable rotors can be formed in rigid materials such as, but not limited to, glass and non-conductive substrates.

Accordingly, in the practice of the invention, external hardware provides the mechanical valving necessary for communication of a miniaturized column device to different external liquid reservoirs, such as an electrolyte solution, flush solution or the sample via laser-ablated holes designed into the cover plate 12. This feature allows a variety of injection methods to be adapted to a miniaturized planar column device constructed according to the invention, including pressure injection, hydrodynamic injection or electrokinetic injection. In the particular embodiment of FIGS. 1–3, it is contemplated that external valving and injection means communicate with the sample processing device by butt-coupling to the laser-ablated apertures, however, any other suitable methods of connection known in the art may easily be adapted to the invention. Further, it is noted that numerous other sample introduction and fluid interfacing designs may be practiced and still fall within the spirit of the subject invention.

Also according to the invention, a wide variety of means for applying a motive force along the length of the sample processing compartment 14 may be associated with the subject device. In this regard, a pressure differential or electric potential may be applied along the entire length of the sample processing compartment by interfacing motive means with inlet port 18 and outlet port 22.

The use of substrates such as polyimides in the construction of miniaturized columns according to the invention allows the possibility of using refractive-index (RI) detection to detect separated analytes of interest passing through the subject columns. In this regard, the provision of an associated laser diode which emits radiation at a wavelength where polyimide is "transparent" (such as at >500 nm) allows for a detection setup where no additional features need to be ablated in the column devices.

Referring now to FIGS. 2–4, in a preferred embodiment of the invention, detection means may be ablated into the substrate 4 and cover plate 12, where said detection means is disposed substantially downstream of the first end 16 of the sample processing compartment 14. More particularly, an aperture 34 may be ablated through substrate 4 to communicate with the sample processing compartment 14. A corresponding aperture 36 may be likewise formed in cover plate 12, and arranged so that it will be in co-axial alignment with aperture 34 when the cover plate is affixed to the substrate to form the sample processing compartment 14. In this manner, electrodes (not shown) may be connected to the miniaturized column device via the apertures 34 and 36 to detect separated analytes of interest passing through the sample processing compartment by electrochemical detection techniques.

Figure 5:
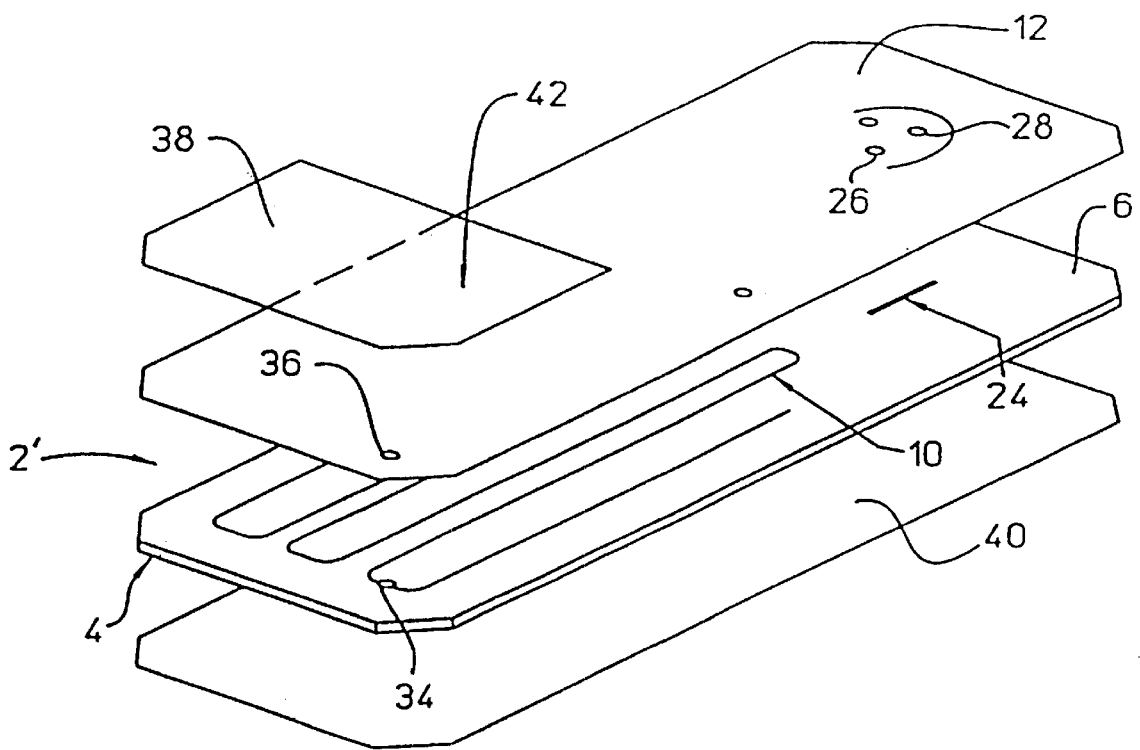
FIG. 5 is an exploded view of a preferred embodiment of the prior art including optical detection means.

Referring to FIG. 5, a further embodiment of the invention, indicated at 2' is shown comprising a preferred detection means indicated generally at 42. More particularly, a first transparent sheet 38 is provided wherein the cover plate 12 is interposed between said first transparent sheet and substrate 4. A second transparent sheet 40 is also provided wherein the second sheet is disposed over the second planar surface 8 of the substrate 4. In this manner, detection means 42 allows optical detection of separated analytes passing through sample processing compartment, formed by the combination of microchannel 10 and cover plate 12, via transmission of radiation orthogonal to the major axis of the sample processing compartment (and, accordingly, orthogonal to the direction of electro-osmotic flow in an electrophoretic separation). Further, in the practice of the invention, the transparent sheets may comprise materials such as quartz, diamond, sapphire, fused silica or any other suitable substrate which enables light transmission therethrough.

The subject transparent sheets may be formed with just enough surface area to cover and seal the detection apertures 34 and 36, or said sheets may be sized to cover up to the entire surface area of the column device. In this regard, additional structural rigidity may be provided to a column device formed in a particularly thin substrate film, such as a thin-film polyimide substrate, by employing a substantially co-planar sheet of, for example, fused silica.

Accordingly, the above described optical detection means 42 enables adaptation of a variety of external optical detection means to miniaturized columns constructed according to the invention. Further, sealing of the transparent sheets 38 and 40 to the miniaturized column device 2' is readily enabled, for example, when substrate 4 and cover plate 12 are formed in polyimide materials which include a layer of a thermal adhesive form of polyimide, since it is known that quartz/Kapton® bonds formed using such adhesives are very resilient. Sealing of other preferred transparent sheet materials, such as diamond, sapphire or fused-silica to the subject device may be accomplished using adhesion techniques well known in the art.

The possibility of detecting with radiation over a range of electromagnetic wavelengths offers a variety of spectrophotometric detection techniques to be interfaced with a miniaturized column according to the invention, including UV/Vis, fluorescence, refractive index (RI) and Raman.

Furthermore, as will be readily appreciated, the use of optical detection means comprising apertures ablated into the substrate and cover plate provides great control over the effective detection path length in a miniaturized column device constructed according to the invention. In this regard, the detection path length will be substantially equal to the combined thickness of the substrate 4 and the cover plate 12, and detection path lengths of up to 250 μm are readily obtainable using the subject detection means 42 in thin-film substrates such as polyimides.

Figure 6:
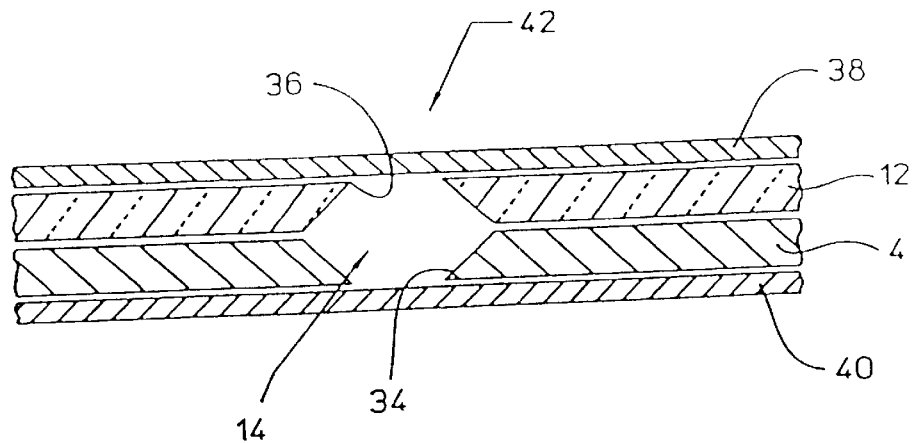
FIG. 6 is a cross-sectional axial view of the intersection of the sample processing compartment and the optical detection means in the prior art miniaturized column device of FIG. 5.

Referring now to FIG. 6, it can be seen that apertures 34 and 36 provide an enlarged volume in sample processing compartment 14 at the point of intersection with the detection means 42, where that volume will be proportional to the combined thickness of substrate 4 and cover plate 12. In this manner, sample plugs passing through sample processing compartment 14 may be subject to untoward distortion as the plug is influenced by the increased compartment volume in the detection area, especially where the combined thickness of the substrate and cover plate exceeds about 250 μm, thereby possibly reducing separation efficiency in the device.

Accordingly, in the present invention wherein detection path lengths exceeding 250 μm are desired, an alternative device embodiment is provided having laser-ablated features on two opposing surfaces of a substrate. More particularly, in FIGS. 7A and 7B, a further embodiment of a miniaturized column device is generally indicated at 52. The miniaturized column comprises a substrate 54 having first and second substantially planar opposing surfaces respectively indicated at 56 and 58. The substrate 54 has a first microchannel 60 laser ablated in the first planar surface 56 and a second microchannel 62 laser ablated in the second planar surface 58, wherein the microchannels can be provided in a wide variety of geometries, configurations and aspect ratios as described above.

Figure 7A:
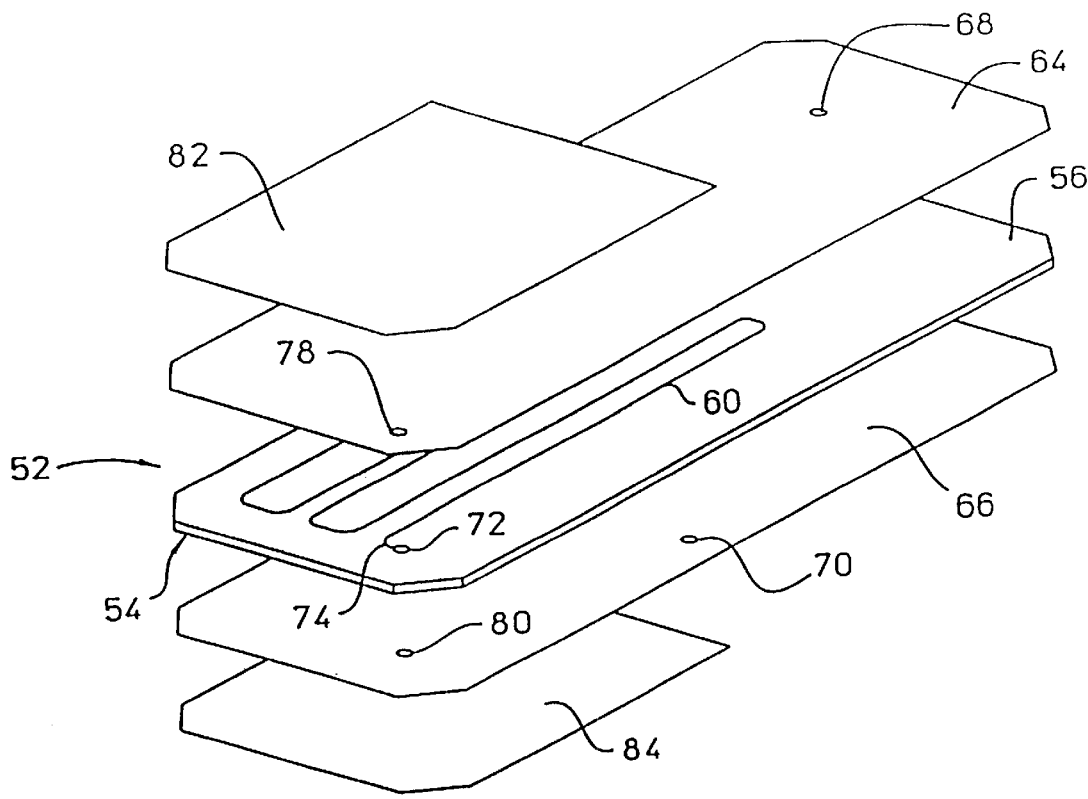
FIG. 7A is an exploded view of a first side of a prior art miniaturized column device having microchannels formed on two opposing planar surfaces of a support substrate.
Figure 7B:
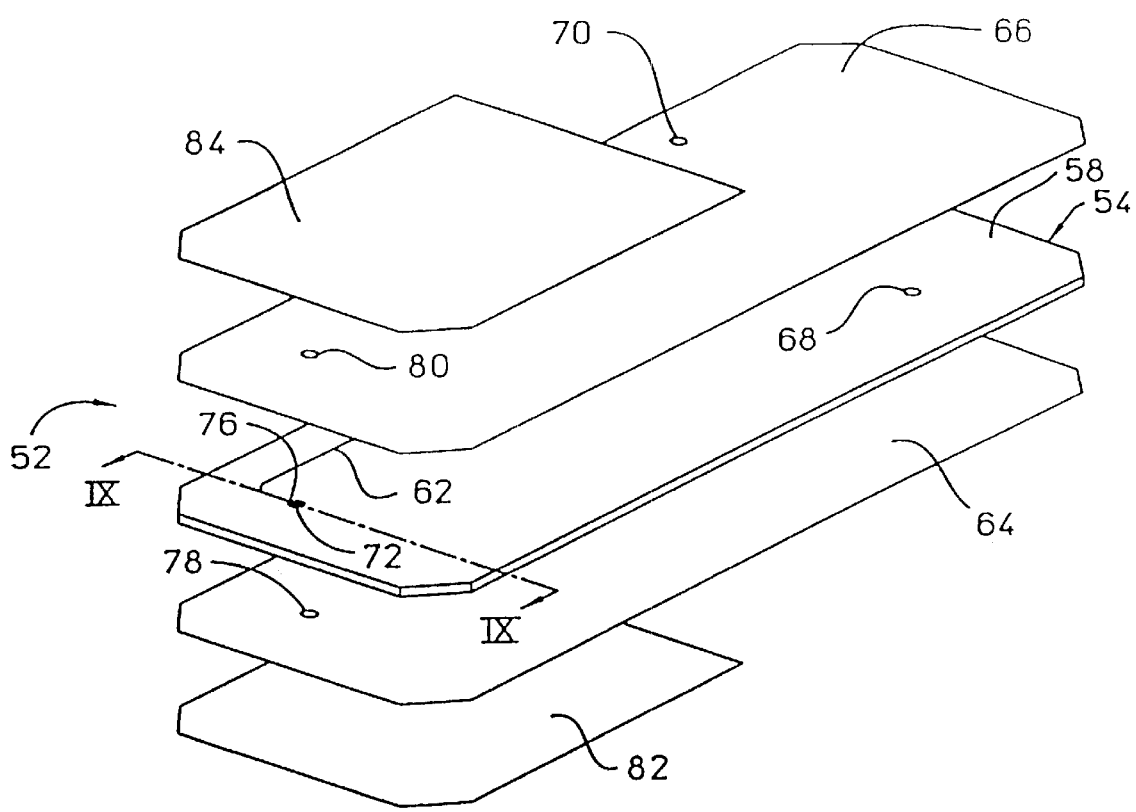
FIG. 7B is an exploded view of a second side of the prior art column device of FIG. 7A.

The miniaturized column device of FIGS. 7A and 7B further includes first and second cover plates, indicated at 64 and 66 respectively, which, in combination with the first and second microchannels 60 and 62, define first and second elongate separation compartments when substrate 54 is sandwiched between the first and second cover plates.

Referring still to FIGS. 7A and 7B, a plurality of apertures can be laser-ablated in the device to provide an extended separation compartment, and further to establish fluid communication means. More particularly, a conduit means 72, comprising a laser ablated aperture in substrate 54 having an axis which is orthogonal to the first and second planar surfaces 56 and 58, communicates a distal end 74 of the first microchannel 60 with a first end 76 of the second microchannel 62 to form an extended separation compartment.

Further, an aperture 68, laser ablated in the first cover plate 64, enables fluid communication with the first microchannel 60, and a second aperture 70, laser ablated in the second cover plate 66, enables fluid communication with the second microchannel 62. As will be readily appreciated, when the aperture 68 is used as an inlet port, and the second aperture 70 is used as an outlet port, a miniaturized column device is provided having a flow path extending along the combined length of the first and second microchannels 60 and 62.

In the embodiment of the invention as shown in FIGS. 7A and 7B, a wide variety of sample introduction means can be employed, such as those described above. External hardware can also be interfaced to the subject device to provide liquid handling capabilities, and a variety of means for applying a motive force along the length of the separation compartment can be associated with the device, such as by interfacing motive means with the first and/or second apertures 68 and 70 as described above.

Additionally, a variety of detection means are easily included in the subject embodiment. In this regard, a first aperture 78 can be laser ablated in the first cover plate 64, and a second aperture 80 can likewise be formed in the second cover plate 66 such that the first and second apertures will be in co-axial alignment with conduit means 72 when the substrate 54 is sandwiched between the first and second cover plates. Detection of analytes in a separated sample passing through the conduit means is thereby easily enabled, such as by connecting electrodes to the miniaturized column via apertures 78 and 80 and detecting using electrochemical techniques.

Figure 9:
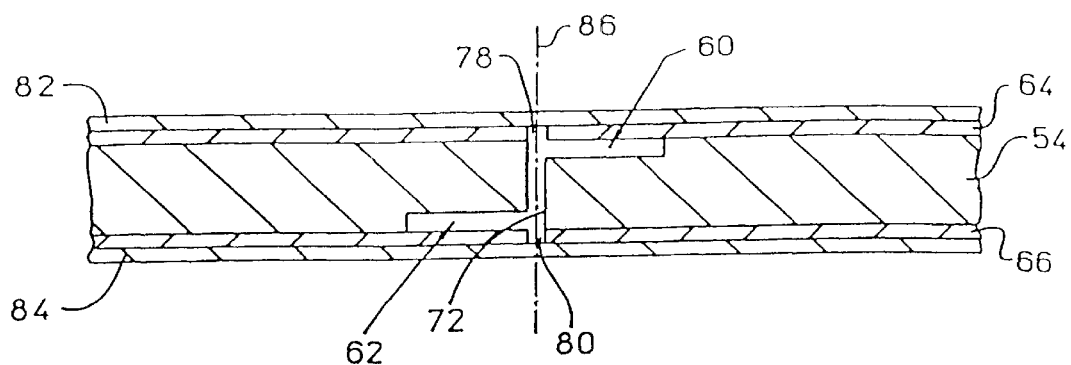
FIG. 9 is a cross-sectional trans-axial view of the extended optical detection path length in the prior art miniaturized column of FIG. 8 taken along lines IX—IX.

However, a key feature of the laser-ablated conduit means 72 is the ability to provide an extended optical detection path length of up to 1 mm, or greater, without experiencing untoward sample plug distortion due to increased separation compartment volumes at the point of detection. Referring to FIGS. 7A, 7B and 9, first and second transparent sheets, indicated at 82 and 84 respectively, can be provided such that the first cover plate 64 is interposed between the first transparent sheet and the first planar surface 56, and the second cover plate 66 is interposed between the second transparent sheet and the second planar surface 58. The transparent sheets 82 and 84 can be selected from appropriate materials such as quartz crystal, fused silica, diamond, sapphire and the like. Further, the transparent sheets can be provided having just enough surface area to cover and seal the apertures 78 and 80, or those sheets can be sized to cover up to the entire surface area of the column device. As described above, this feature allows additional structural rigidity to be provided to a column device formed in a particularly thin substrate.

As best shown in FIG. 9, the subject arrangement allows optical detection of sample analytes passing through the miniaturized column device to be carried out along an optical detection path length 86 corresponding to the major axis of the conduit means 72. As will be readily appreciated, the optical detection path length 86 is substantially determined by the thickness of the substrate 54, and, accordingly, a great deal of flexibility in tailoring a miniaturized column device having $\mu$-meter column dimensions and optical path lengths of up to 1 mm or greater is thereby enabled under the instant invention. In this manner, a wide variety of associated optical detection devices may be interfaced with a miniaturized column constructed according to the invention, and detection of analytes in samples passing through the conduit means 72 may be carried out using UV/Vis, fluorescence, refractive index (RI), Raman and like spectrophotometric techniques.

Figure 8A:
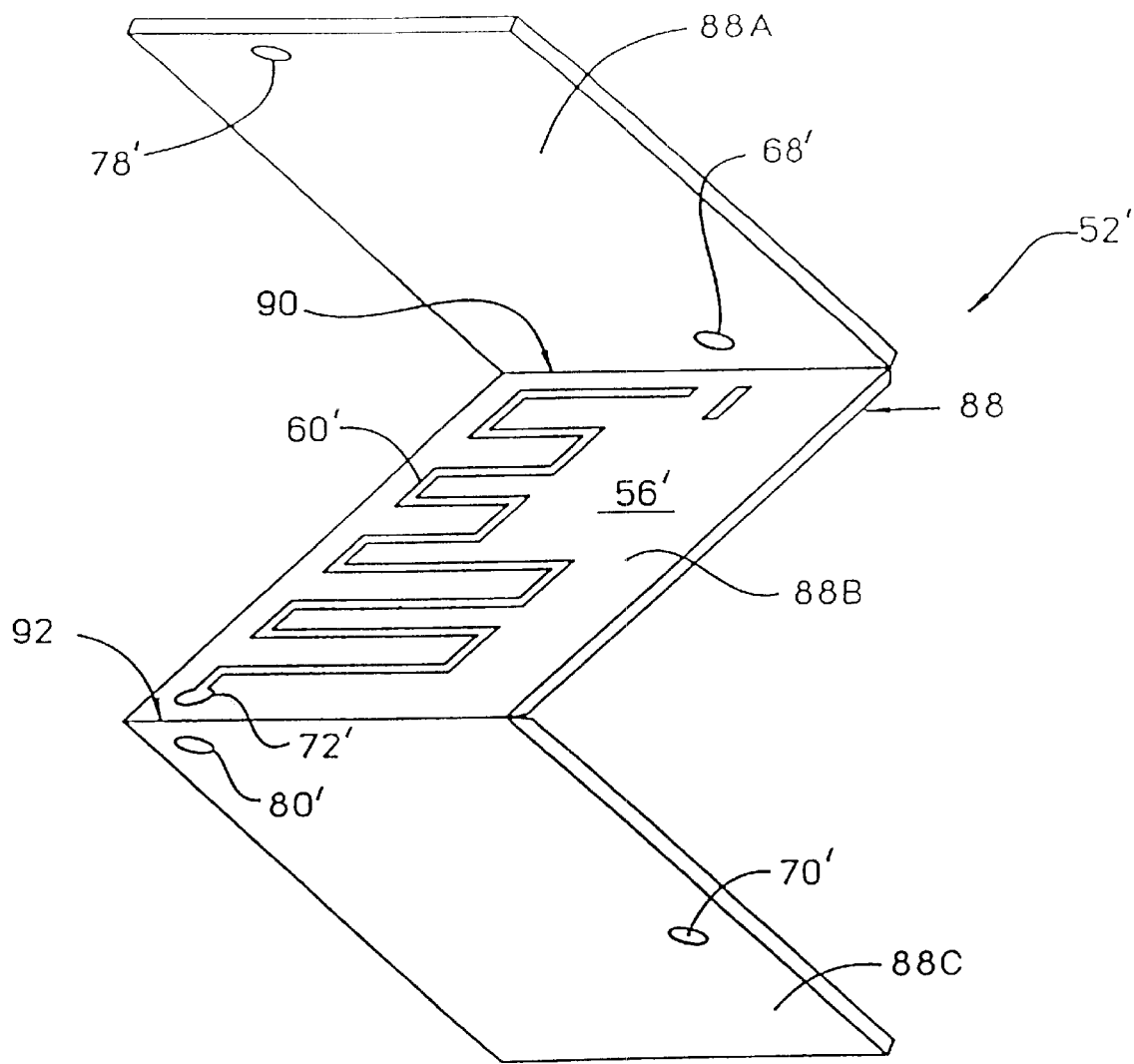
FIG. 8A is a pictorial representation of a first side of a preferred embodiment of the prior art miniaturized column device of FIG. 7A which is constructed from a single flexible substrate.
Figure 8B:
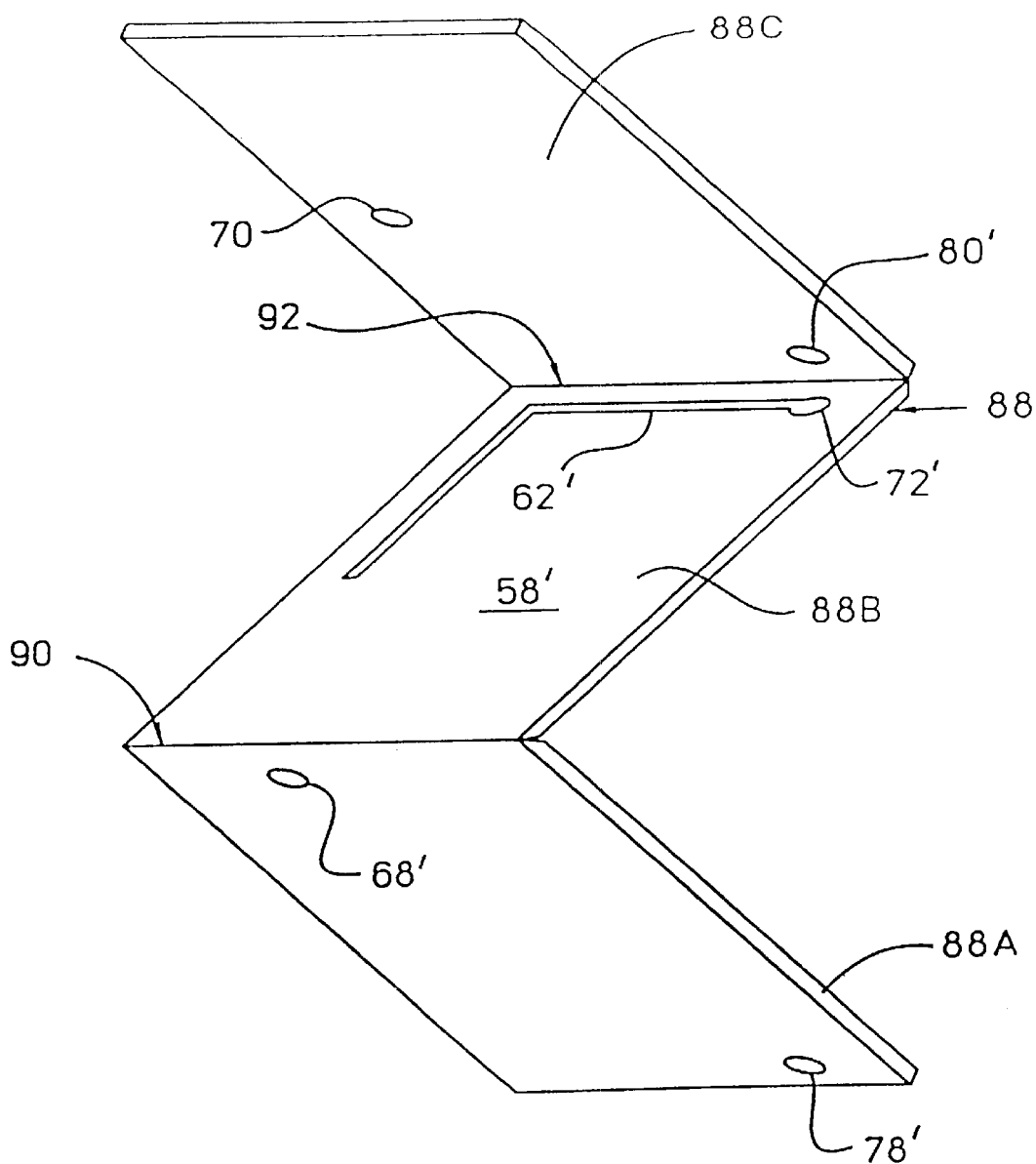
FIG. 8B is a pictorial representation of a second side of the prior art column device of FIG. 8A.

Referring now to FIGS. 8A and 8B, a related embodiment of the invention is shown, comprising a miniaturized column device 52', wherein the column portion and the first and second cover plates are formed in a single, flexible substrate generally indicated at 88. The flexible substrate 88 thus comprises three distinct regions, a column portion 88B, having first and second substantially planar opposing surfaces 56' and 58', respectively, where the column portion is interposed between a first cover plate portion 88A and a second cover plate portion 88C. The first and second cover plate portions have at least one substantially planar surface. The first cover plate portion 88A and the column portion 88B are separated by at least one fold means 90 such that the first cover plate portion can be readily folded to overlie the first substantially planar surface 56' of the column portion 88B. The second cover plate portion 88C and the column portion 88B are likewise separated by at least one fold means 92 such that the second cover plate can be readily folded to overlie the second substantially planar surface 58' of the column portion 88B. In particularly preferred embodiments, each fold means 90 and 92 can comprise a row of spaced-apart perforations ablated in the flexible substrate, spaced-apart slot-like depressions or apertures ablated so as to extend only part way through the substrate, or the like. The perforations or depressions can have circular, diamond, hexagonal or other shapes that promote hinge formation along a predetermined straight line.

Thus, the miniaturized column device 52' is formed by laser ablating a first microchannel 60' in the first planar surface 56' of the column portion 88B, and a second microchannel 62' in the second planar surface 58' of the column portion. Each microchannel can be provided in a wide variety of geometries, configurations and aspect ratios. A first separation compartment is then formed by folding the flexible substrate 88 at the first fold means 90 such that the first cover plate portion 88A covers the first microchannel 60' to form an elongate separation compartment. A second separation compartment is then provided by folding the flexible substrate 88 at the second fold means 92 such that the second cover plate portion 88C covers the second microchannel 62' to form a separation compartment as described above. A conduit means 72', comprising a laser ablated aperture in the column portion 88B having an axis which is orthogonal to the first and second planar surfaces 56' and 58', communicates a distal end of the first microchannel 60' with a first end of the second microchannel 62' to form a single, extended separation compartment.

Further, an aperture 68', laser ablated in the first cover plate portion 88A, enables fluid communication with the first microchannel 60', and a second aperture 70', laser ablated in the second cover plate portion 88C, enables fluid communication with the second microchannel 62'. As described above, when the first and second apertures are used as an inlet and outlet port, respectively, a miniaturized column device is provided having a flow path extending along the combined length of the first and second microchannels.

Detection means can optionally be included in the device of FIGS. 8A and 8B. In one particular embodiment, a first aperture 78' can be laser ablated in the first cover plate portion 88A, and a second aperture 80' can likewise be formed in the second cover plate portion 88C, wherein the apertures are arranged to co-axially communicate with each other and communicate with the conduit means 72' when the flexible substrate 88 is hingeably folded as described above to accurately align the apertures 78' and 80' with the conduit means 72'.

In yet further related aspects of the invention, optional micro-alignment means—formed either by laser ablation techniques or by other methods of fabricating shaped pieces well known in the art—are provided in the miniaturized column device 52'. More specifically, a plurality of corresponding laser-ablated apertures (not shown) can be provided in the column portion 88B and the first and second cover plate portions, 88A and 88C, respectively of the flexible substrate 88. The subject apertures are arranged such that co-axial alignment thereof enables the precise alignment of the column portion with one, or both of the cover plate portions to align various features such as the optional detection means with the ablated conduit. Such optional alignment can be effected using an external apparatus with means (such as pins) for cooperating with the co-axial apertures to maintain the components are portions in proper alignment with each other.

Accordingly, novel miniaturized column devices have been described which are laser ablated into a substrate other than silicon or silicon dioxide materials, and which avoid several major problems which have come to be associated with prior attempts at providing micro-column devices. The use of laser ablation techniques in the practice of the invention enables highly symmetrical and accurately defined micro-column devices to be fabricated in a wide class of polymeric and ceramic substrates to provide a variety of miniaturized liquid-phase analysis systems. In this regard, miniaturized columns may be provided which have microcapillary dimensions (ranging from 5–200 $\mu$m in diameter) and column detection path lengths of up to 1 mm or greater. This feature has not been attainable in prior attempts at miniaturization, such as in capillary electrophoresis, without substantial engineering of a device after capillary formation. Further, laser ablation of miniaturized columns in inert substrates such as polyimides avoids the problems encountered in prior devices formed in silicon or silicon dioxide-based materials. Such problems include the inherent chemical activity and pH instability of silicon and silicon dioxide-based substrates which limits the types of separations capable of being performed in those devices.

In the practice of the invention, miniaturized column devices may be formed by laser ablating a set of desired features in a selected substrate using a step-and-repeat process to form discrete units. In this regard, it is particularly contemplated to laser ablate the subject devices in condensation polymer substrates including polyimides, polyamides, poly-esters and poly-carbonates. Further, the instant invention may be practiced using either a laser ablation process or a LIGA process to form templates encompassing a set of desired features, whereby multiple copies of miniaturized columns may be mass-produced using injection molding techniques well known in the art. More particularly, it is contemplated herein to form miniaturized columns by injection molding in substrates comprised of materials such as the following: polycarbonates; polyesters, including poly(ethylene terephthalate) and poly(butylene terephthalate); polyamides, (such as nylons); polyethers, including polyformaldehyde and poly(phenylene sulfide); polyimides, such as Kapton® and Upilex®; polyolefin compounds, including ABS polymers, Kel-F copolymers, poly(methyl methacrylate), poly(styrene-butadiene) copolymers, poly(tetrafluoroethylene), poly(ethylene-vinyl acetate) copolymers, poly(N-vinylcarbazole) and polystyrene.

Laser ablation of microchannels in the surfaces of the above-described substrates has the added feature of enabling a wide variety of surface treatments to be applied to the microchannels before formation of the sample processing compartment. That is, the open configuration of laser-ablated microchannels produced using the method of the invention enables a number of surface treatments or modifications to be performed which are not possible in closed format constructions, such as in prior micro-capillaries. More specifically, laser ablation in condensation polymer substrates provides microchannels with surfaces featuring functional groups, such as carboxyl groups, hydroxyl groups and amine groups, thereby enabling chemical bonding of selected species to the surface of the subject microchannels using techniques well known in the art. Other surface treatments enabled by the open configuration of the instant devices include surface adsorptions, polymer graftings and thin film deposition of materials such as diamond or sapphire to microchannel surfaces using masking and deposition techniques and dynamic deactivation techniques well known in the art of liquid separations.

The ability to exert rigid computerized control over the present laser ablation processes enables extremely precise microstructure formation, which, in turn, enables the formation of miniaturized columns having features ablated in two substantially planar components wherein those components may be aligned to define a composite sample processing compartment of enhanced symmetry and axial alignment. In this regard, it is contemplated to provide a further embodiment of the invention wherein laser ablation is used to create two component halves which, when folded or aligned with one another, define a single miniaturized column device.

Figure 10:
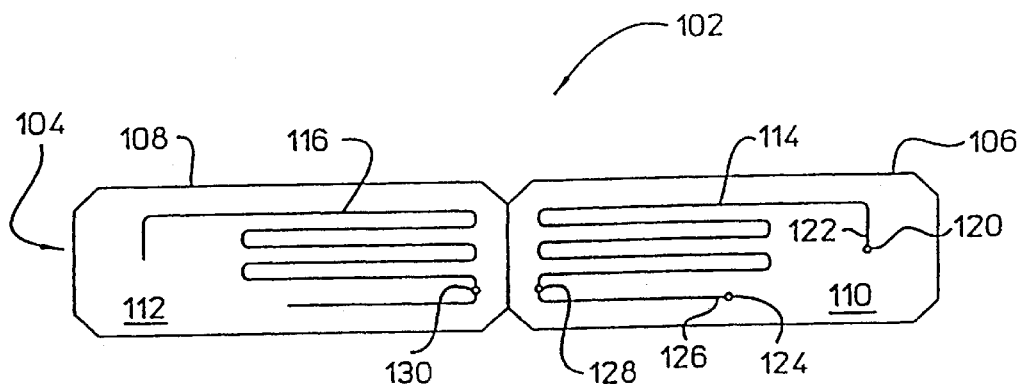
FIG. 10 is plan view of a prior art miniaturized column device constructed according to the invention having first and second component halves.

Referring now to FIG. 10, a miniaturized column for liquid phase analysis of a sample is generally indicated at 102. The miniaturized column 102 is formed by providing a support body 104 having first and second component halves indicated at 106 and 108 respectively. The support body may comprise a substantially planar substrate such as a polyimide film which is both laser ablatable and flexible so as to enable folding after ablation; however, the particular substrate selected is not considered to be limiting in the invention.

The first and second component halves 106 and 108 each have substantially planar interior surfaces, indicated at 110 and 112 respectively, wherein miniaturized column features may be laser ablated. More particularly, a first microchannel pattern 114 is laser ablated in the first planar interior surface 110 and a second microchannel pattern 116 is laser ablated in the second planar interior surface 112. According to the invention, said first and second microchannel patterns are ablated in the support body 104 so as to provide the mirror image of each other.

Figure 11:
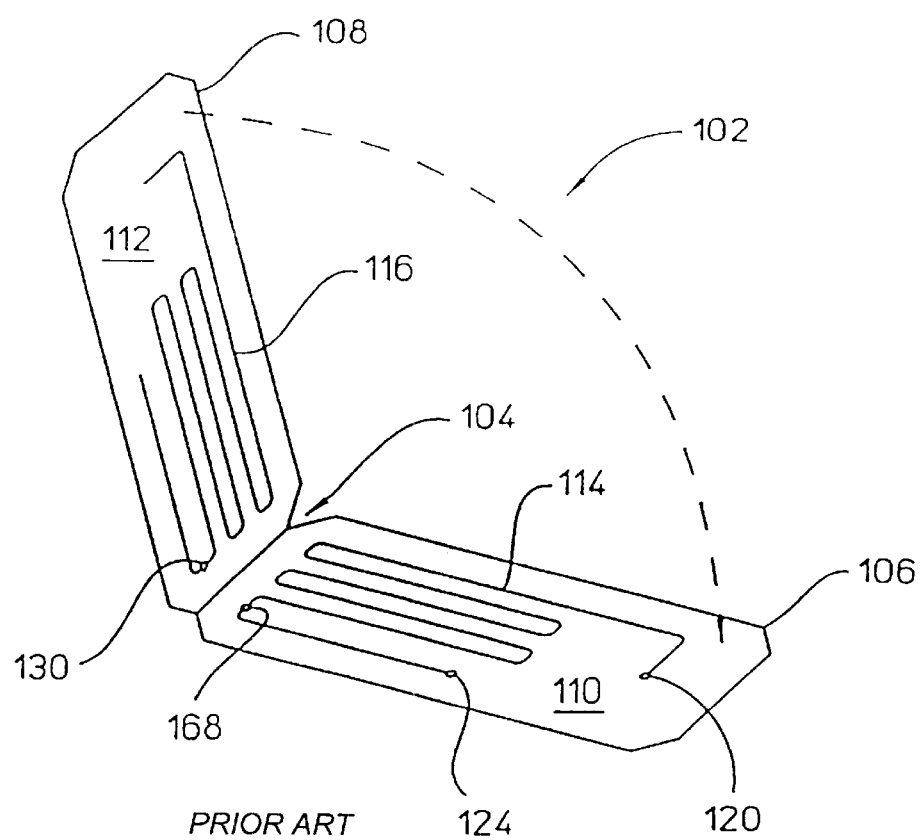
FIG. 11 is a pictorial representation of the prior art column device of FIG. 10 showing the folding alignment of the component halves to form a single device.
Figure 12:
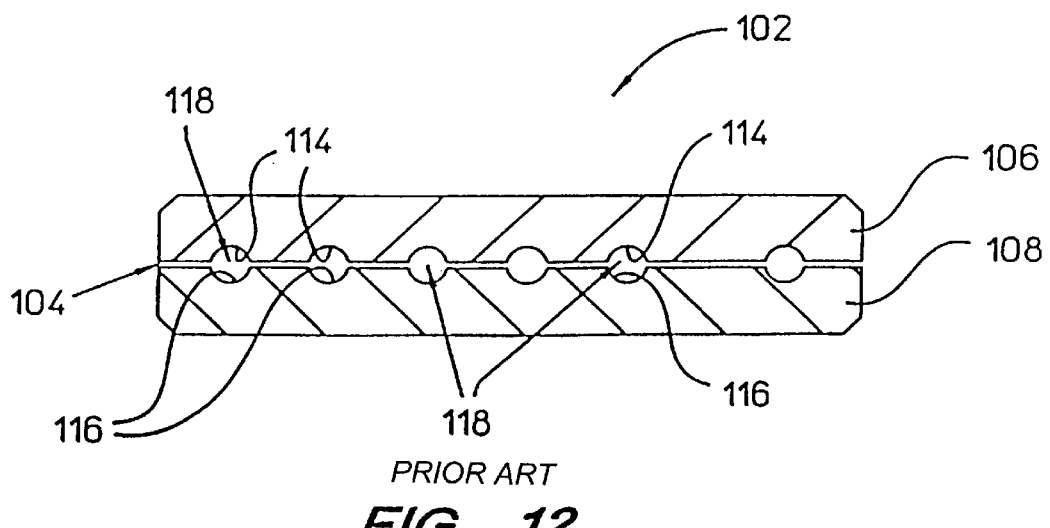
FIG. 12 is a cross-sectional axial view of the sample processing compartment formed by the alignment of the component halves in the prior art device of FIG. 10

Referring now to FIGS. 11 and 12, a sample processing compartment 118, comprising an elongate bore defined by the first and second microchannel patterns 114 and 116 may be formed by aligning (such as by folding) the first and second component halves 106 and 108 in facing abutment with each other. In the practice of the invention, the first and second component halves may be held in fixable alignment with one another to form a liquid-tight sample processing compartment using pressure sealing techniques, such as by application of tensioned force, or by use of adhesives well known in the art of liquid phase separation devices. It is further contemplated according to the invention to form first and second microchannels 114 and 116 having semi-circular cross-sections whereby alignment of the component halves defines a sample processing compartment 118 having a highly symmetrical circular cross-section to enable enhanced fluid flow therethrough; however, as discussed above, a wide variety of microchannel geometries are also within the spirit of the invention.

In a further preferred embodiment of the invention, it is particularly contemplated to form the support body 104 from a polymer laminate substrate comprising a Kapton® film co-extruded with a thin layer of a thermal plastic form of polyimide referred to as KJ® and available from DuPont (Wilmington, Del.). In this manner, the first and second component halves 106 and 108 may be heat sealed together, resulting in a liquid-tight weld that has the same chemical properties and, accordingly, the same mechanical, electrical and chemical stability, as the bulk Kapton® material.

Referring now to FIGS. 10–12, the miniaturized column device 102 further comprises means for communicating associated external fluid containment means (not shown) with the sample processing compartment 118 to provide a liquid-phase separation device. More particularly, a plurality of apertures may be laser ablated in the support body 104, wherein said apertures extend from at least one exterior surface of the support body and communicate with at least one microchannel, said apertures permitting the passage of fluid therethrough. In this regard, an inlet port 120 may be laser ablated in the first component half 106 and communicate with a first end 122 of said first microchannel 114. In the same manner, an outlet port 124 may be ablated in the first component half and communicate with a second end 126 of said first microchannel 114.

As is readily apparent, a liquid phase sample processing device may thereby be formed, having a flow path extending from the first end 122 of the microchannel 114 to the second end 126 thereof, by communicating fluids from an associated source (not shown) through the inlet port 120, passing the fluids through the sample processing compartment 118 formed by the alignment of microchannels 114 and 116, and allowing the fluids to exit the sample processing compartment via the outlet port 126. In this manner, a wide variety of liquid phase analysis procedures may be carried out in the subject miniaturized column device using techniques well known in the art. Furthermore, various means for applying a motive force along the length of the sample processing compartment 118, such as a pressure differential or electric potential, may be readily interfaced to the column device via the inlet and outlet ports, or by interfacing with the sample processing compartment via additional apertures which may be ablated in the support body 104.

Inlet port 120 may be formed such that a variety of external fluid and/or sample introduction means may be readily interfaced with the miniaturized column device 102. As discussed in greater detail above, such means include external pressure injection, hydrodynamic injection or electrokinetic injection mechanisms.

Referring now to FIGS. 10 and 11, the miniaturized column device 102 further comprises detection means laser ablated in the support body 104. More particularly, a first aperture 128 is ablated in said first component half 106 and communicates with the first microchannel 114 at a point near the second end 126 thereof. A second aperture 130 is likewise formed in said second component half 108 to communicate with the second microchannel 116. Accordingly, a wide variety of associated detection means, e.g., NMR detection means (see, U.S. application Ser. No. 09/106,495), now U.S. Pat. No. 6,194,950 may then be interfaced to the sample processing compartment 118 to detect separated analytes of interest passing therethrough, such as by connection of electrodes to the miniaturized column via the first and second apertures 128 and 130.

In yet a further preferred embodiment of the invention, an optical detection means is provided in the miniaturized column device 102. In this regard, first and second apertures 128 and 130 may be ablated in the support body 104 such that when the component halves are aligned to form the sample processing compartment 118 said apertures are in co-axial alignment with one another, said apertures further having axes orthogonal to the plane of said support body. As will be readily appreciated by one of ordinary skill in the art, by providing transparent sheets (not shown), disposed over the exterior of the support body 104 and covering said first and second apertures 128 and 130, a sample passing through sample processing compartment 118 may be analyzed by interfacing spectrophotometric detection means with said sample through the transparent sheets using techniques well known in the art. The optical detection path length may be substantially determined by the combined thickness of said first and second component halves 106 and 108. In this manner, an optical detection path length of up to 250 $\mu$m is readily provided by ablating the miniaturized column device in a 125 $\mu$m polymer film.

Accordingly, there have been described several preferred embodiments of a miniaturized column device formed according to the invention by laser ablating microstructures on component parts and aligning the components to form columns having enhanced symmetries. As described in detail above, formation of the subject microchannels in the open configuration enables a wide variety of surface treatments and modifications to be applied to the interior surfaces of the channels before formation of the sample processing compartment. In this manner, a wide variety of liquid phase analysis techniques may be carried out in the composite sample processing compartments thus formed, including chromatographic, electrophoretic and electrochromatographic separations.

In the practice of the invention, it is further contemplated to provide optional means for the precise alignment of component support body halves, thereby ensuring accurate definition of a composite sample processing compartment formed according to the invention. More particularly, in a further preferred embodiment of the invention, micro-alignment means are provided to enable enhanced alignment of laser-ablated component parts such as microchannels, detection apertures and the like.

Figure 13:
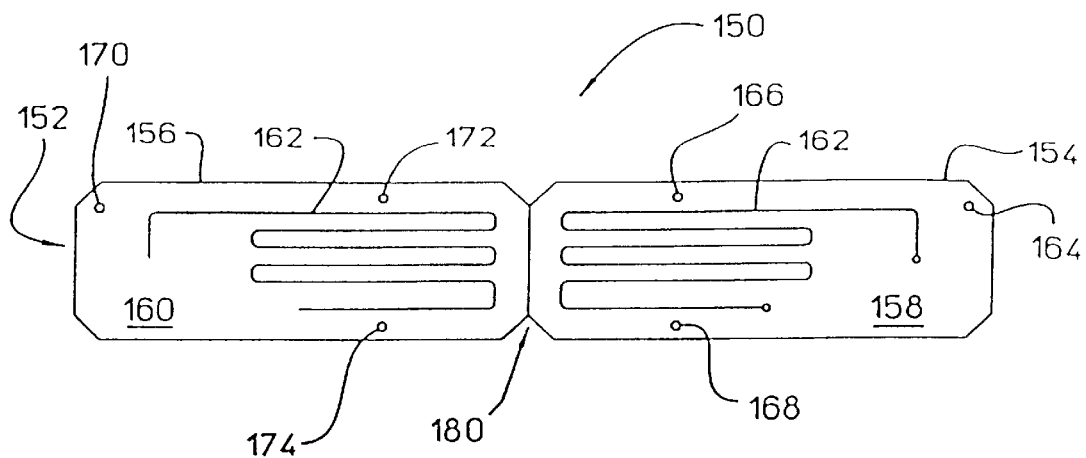
FIG. 13 is a plan view of a further prior art embodiment of the present invention having optional micro-alignment means on first and second component halves.
Figure 14:
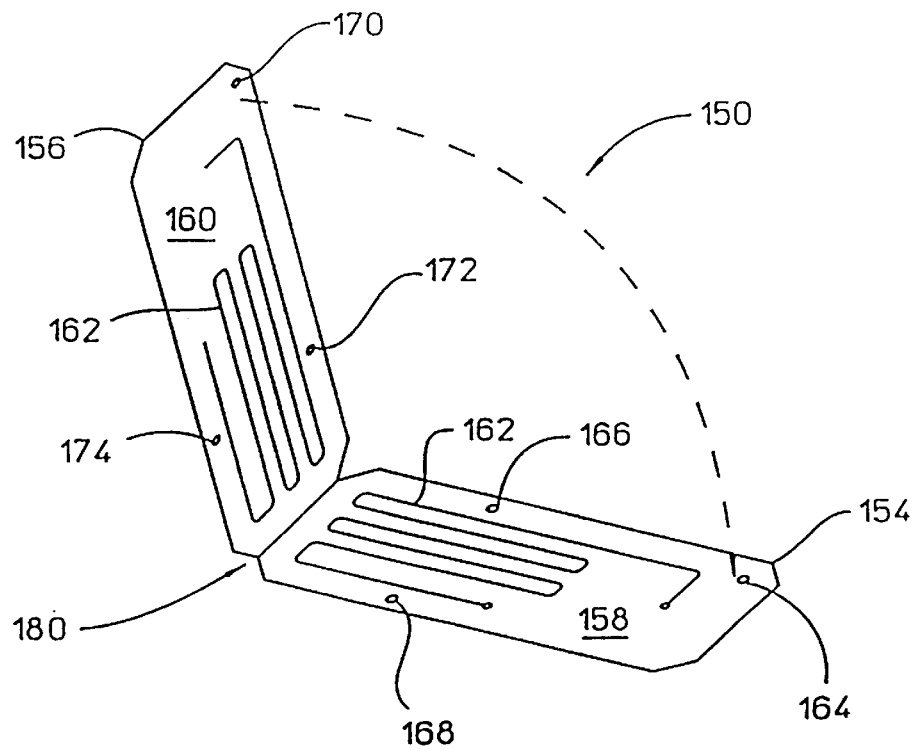
FIG. 14 is a pictorial representation of the prior art column device of FIG. 13 showing the micro-alignment of the component halves.

Referring now to FIGS. 13 and 14, a miniaturized column device constructed according to the present invention is generally indicated at 150 and is formed in a flexible substrate 152. The column device comprises first and second support body halves, indicated at 154 and 156 respectively, each having a substantially planar interior surface indicated at 158 and 160 respectively. The interior surfaces comprise laser-ablated microstructures, generally indicated at 162, where said microstructures are arranged to provide the mirror image of one another in the same manner as described in greater detail above.

The accurate alignment of component parts may be enabled by forming a miniaturized column device in a flexible substrate 152 having at least one fold means, generally indicated at 180, such that a first body half 154 may be folded to overlie a second body half 156. The fold means 180 may comprise a row of spaced apart perforations ablated in the substrate 152, spaced-apart slot-like depressions or apertures ablated so as to extend only part way through the substrate, or the like. The perforations or depressions may have circular, diamond, hexagonal or other shapes that promote hinge formation along a predetermined straight line.

Accordingly, in the practice of the invention, the fold means 180 allows said first and second support body halves 154 and 156 to hingeably fold upon one another and accurately align composite features defined by said microstructures ablated on said first and second planar interior surfaces 158 and 160.

It is further contemplated to provide additional micro-alignment means formed either by laser ablation or by other methods of fabricating shaped pieces well known in the art. More specifically, a plurality of laser-ablated apertures (not shown) may be provided in said first and second support body halves 154 and 156 where said apertures are so arranged such that co-axial alignment thereof enables the precise alignment of the support body halves to define composite features such as an ablated elongate bore. Alignment may be effected using an external apparatus with means (such as pins) for cooperating with said co-axial apertures to maintain the body halves in proper alignment with one another.

Referring to FIGS. 13 and 14, in yet another particular embodiment of the invention, micro-alignment means may been formed in said first and second support body halves 154 and 156 using fabrication techniques well known in the art e.g., molding or the like. In this manner, a plurality of projections, indicated at 164, 166 and 168, may be formed in said first support body half 154. A plurality of depressions, indicated at 170, 172 and 174, may be formed in said second support body half 156.

Accordingly, as is readily apparent, the micro-alignment means are configured to form corresponding structures with one another, whereby projection 164 mates with depression 170, projection 166 mates with depression 172, and projection 168 mates with depression 174 when said support body halves are aligned in facing abutment with one another. In this manner, positive and precise alignment of support body halves 154 and 156 is enabled, thereby accurately defining composite features defined by said laser-ablated microstructures 162.

As will be readily apparent to one of ordinary skill in the art after reading this specification, a wide variety of corresponding micro-alignment features may be formed in the subject miniaturized column devices without departing from the spirit of the instant invention. Such additional features include any combination of holes and/or corresponding structures such as grooves and ridges in said component parts where said features cooperate to enable precise alignment of the component body parts.

Figure 15:
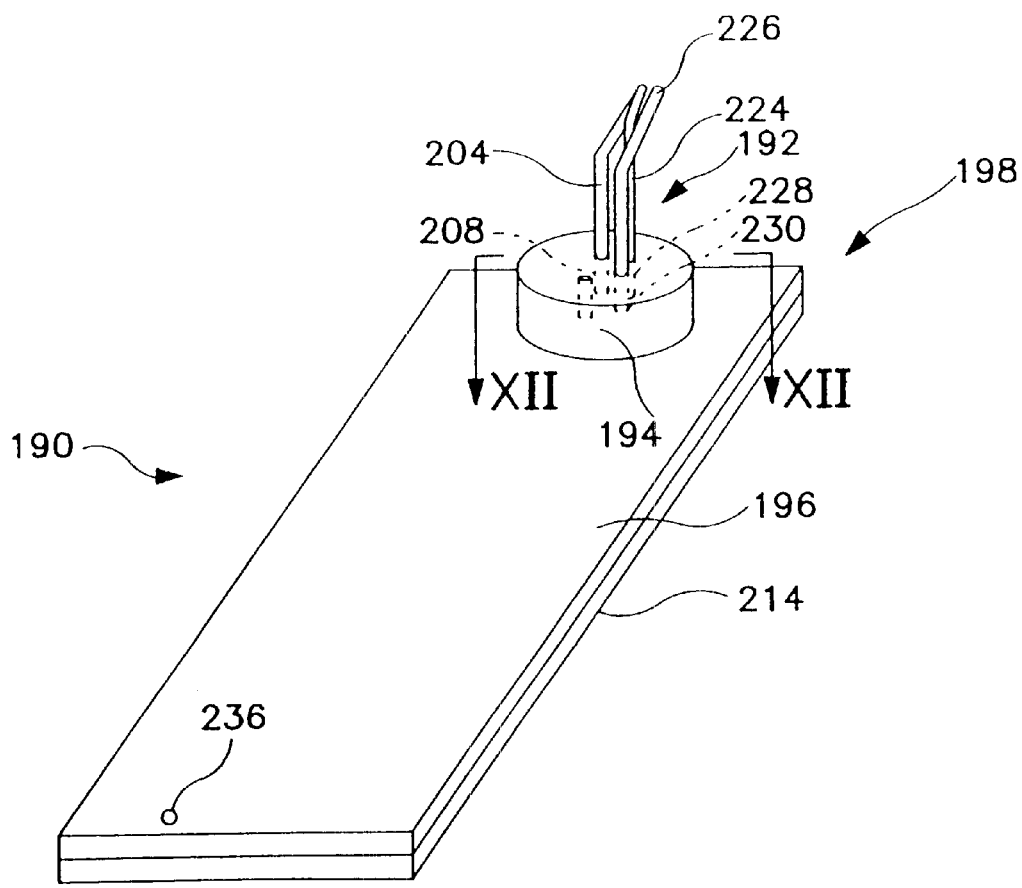
FIG. 15 is a pictorial representation of a liquid phase separation apparatus that includes an externally arranged injection means interfaced with the column device.
Figure 16:
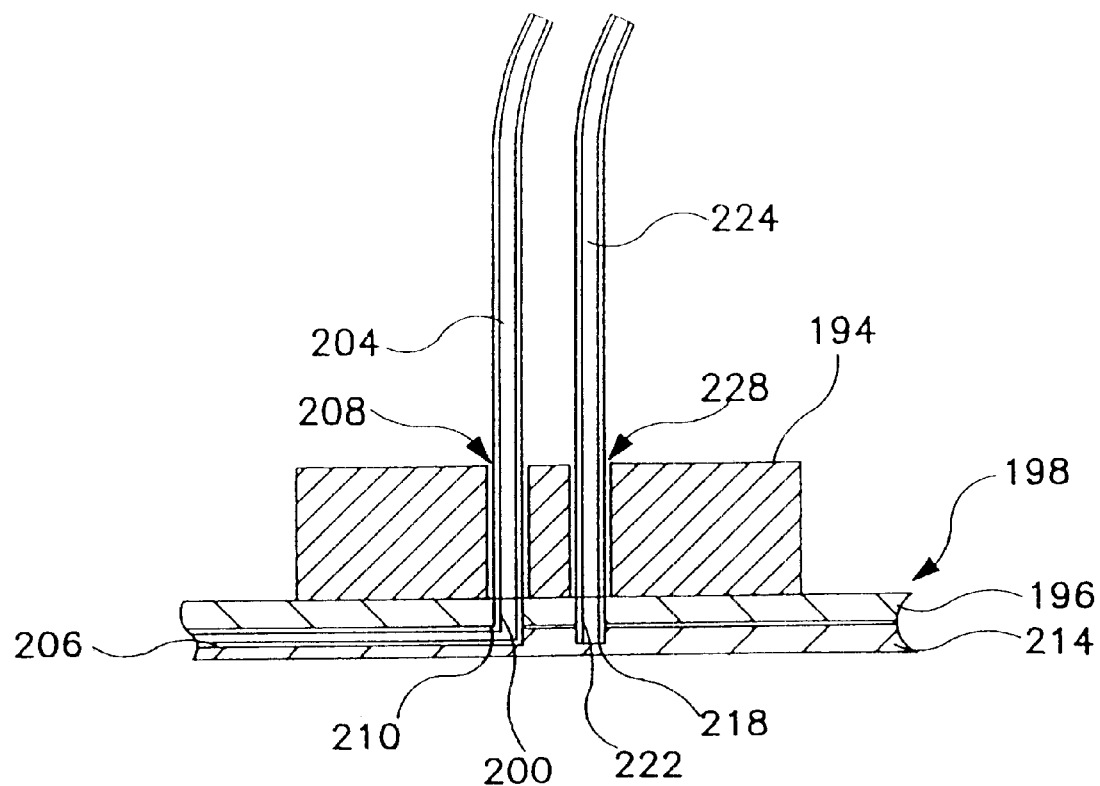
FIG. 16 is a cross-sectional view of the injection means of FIG. 15 taken along lines XII—XII.

Referring now to FIGS. 15 and 16, the apparatus 190 further includes an injection means, generally indicated at 192, which allows for the distribution of externally housed liquid samples, buffers, reagents, and makeup flow fluids into the separation compartment and/or the makeup flow compartment. Thus, in one configuration, the sample introduction means can comprise a manifold 194 that closely engages the cover plate 196 of the miniaturized column device 198, and enables the interface of associated conduits and fluid containment means with the inlet port 200 and/or the makeup fluid inlet 202.

The manifold 194 can be coupled to the cover plate 196 to form a liquid-tight interface using pressure sealing techniques known in the art. The manifold and cover plate can be mechanically urged together using clips, tension springs or any suitable clamping means known in the art. The manifold 194 generally includes a plurality of ports that are configured to correspond with the pattern of apertures and inlets present in the cover plate 196. Referring particularly to FIG. 16, a first conduit 204 can be used to interface an associated containment means (not shown) housing a sample to be separated, or a suitable buffer, with the separation channel 206. The conduit 204 is interposed within a port 208 in the manifold 194, and arranged to be in fluid communication with the upstream terminus 210 of the separation channel 206 via the inlet port 200. In this manner, fluids from the associated containment means can be readily delivered to the separation compartment using known injection methods.

The liquid phase separation apparatus 190 can include a column 198 having an optional bypass microchannel 212 laser-ablated in the substrate 214, whereby a volumetric sample compartment is formed in combination with the cover plate 196. The bypass microchannel has first and second termini, 216 and 218, which respectively cooperate with first and second laser-ablated apertures 220 and 222 that are arranged in the cover plate 196 to correspond with the subject termini when the cover plate is aligned over the substrate 214.

Second and third conduit means, 224 and 226, are respectively interposed within ports 228 and 230 in the manifold 194, whereby the conduit means communicate with the bypass microchannel 212 at the first and second termini, 216 and 218, via the first and second laser-ablated apertures 220 and 222. A sample plug having the dimensions of the volumetric sample compartment is thus provided by passing sample through the compartment from an associated containment means using the conduits 224 and 226 to provide a sample flow path to and from the containment means. By manually removing conduits 204, 224 and 226 from the manifold 194, and coupling manifold ports 228 and 208 together by way of a single conduit, a new flow path is provided that passes from the volumetric sample compartment to the upstream terminus 210 of the separation compartment. By coupling the manifold port 230 with a further conduit means that is in fluid communication with a second associated containment means housing a suitable liquid medium, the sample plug can be flushed from the volumetric sample compartment and delivered into the separation compartment by conveying medium from the second containment means to the manifold using known fluid injection methods.

Once the sample has been delivered to the separation compartment, various means for applying a motive force along the length of the separation compartment can be interfaced to the column device 304 using the manifold 306. Particularly, a pressure differential or electric potential can be established along the length of the separation compartment by coupling an external motive means to the upstream terminus of the separation channel via a manifold port.

The liquid phase separation apparatus 190 may further include detection means, disposed in the cover plate 196 and/or the substrate portion 214. The detection means can comprise one or more apertures or features that have been laser-ablated in the cover plate or substrate portion, e.g., an NMR detection chamber, and communicate with the separation compartment at a position adjacent to, or substantially nearby, the downstream terminus 232 of the separation channel 206 to enable the detection of separated analytes. Referring to FIGS. 10 and 11, one particular apparatus includes an aperture 234 that is ablated in the substrate portion 214 and communicates with the separation channel 206 near the downstream terminus 232 thereof. A second aperture 236 is ablated in the cover plate 196, and is arranged to be in coaxial alignment with the aperture 234 when the cover plate is aligned over the substrate as has been described above. The coaxial apertures allow electrodes to be connected to the miniaturized column device 198 via the subject corresponding apertures to detect separated analytes of interest passing through the separation compartment by electrochemical detection techniques. In one particular apparatus, the coaxially aligned apertures form an optical detection path, enabling the optical detection of separated analytes passing through the separation compartment. As will be appreciated by those skilled in the art, an NMR detection device and/or a wide variety of associated optical detection devices can be interfaced with the separation compartment via the coaxial apertures, enabling the practice of spectrophotometric techniques such as UV/Vis, fluorescence, refractive index (RI), Raman and the like to detect separated analytes in the liquid sample.

A liquid phase separation apparatus can also be designed to have a manifold means that is movable between a plurality of positions relative to a miniaturized planar column device. Referring now to FIGS. 13, 14 and 15A–C, an apparatus 302 is depicted which includes a miniaturized column device 304 as described herein, and a movable manifold means 306 detachably coupled to the column device 304 and arranged near the upstream terminus 308 of a separation channel 310 that has been laser-ablated in a planar surface 312 of the column substrate 314. A cover plate 316 is arranged over the planar surface 312 of the column substrate, and, in combination with the separation channel 310, forms a separation compartment. An inlet port 318, formed from an aperture laser-ablated in the cover plate 316, communicates with the upstream terminus 308 of the separation channel when the cover plate is positioned over the column substrate.

The column device 304 also includes a makeup flow channel 320 laser-ablated in the planar surface 312. A makeup flow compartment is formed by the combination of the cover plate 316 and the makeup flow microchannel 320. The makeup flow channel has an upstream terminus, 322, which is in fluid communication with a makeup inlet port 324, comprising an aperture laser-ablated in the cover plate 316 and arranged to communicate with the terminus when the cover plate is positioned over the column substrate.

The manifold 306 includes a plurality of ports that are configured to correspond with various apertures and inlets present in the cover plate 316 when the manifold is moved between positions relative to the column device 304. In one particular apparatus, the movable manifold 306 comprises a rotor that is butt-coupled to a stator (not shown) present on the external surface of the miniaturized column device 304, whereby the rotor is capable of moving about the stator between selected positions relative to the column device. When the column device is formed in a polyimide substrate, a ceramic rotor, pressed to the device using tensioned force (to form a liquid-tight seal), is capable of rotating between selected aperture positions on the device due to the friction characteristics of the two materials. Other suitable rotors can be formed in rigid materials such as glass and other non-conductive substrates.

Referring particularly to FIG. 14, the manifold 306 includes a first port 326, a second port 328, a third port 330 and a fourth port 332, each port being configured to accept an associated conduit means 334, 336, 338, and 340, respectively. The conduit means are in fluid communication with associated fluid containment means (not shown), such that a fluid sample, reagent or buffer can be communicated to the various ports in the manifold 306 for delivery into the column device 304. Referring now to FIGS. 14 and 15A, when the manifold 306 is in a first position, the first manifold port 326 is in fluid communication with the upstream terminus 308 of the separation channel 310. In this position, a suitable liquid medium, such as an equilibrating buffer or a flush solution, can be delivered into the separation compartment (at the upstream terminus 308) from an associated containment means via the conduit means 334. Further, when the manifold is in the first position, the third manifold port 330 is in fluid communication with the upstream terminus of the makeup flow channel 320. Thus, a suitable liquid medium can be delivered into the makeup flow compartment (at the upstream terminus 322) from the same, or a different associated containment means, via the conduit means 338.

Referring now to FIGS. 14 and 15B, when the manifold 306 has been rotated counter-clockwise about the stator to a second position relative the column device 304, the fourth manifold port 332 is brought into fluid communication with the upstream terminus 308 of the separation channel 310. Accordingly, a volume or aliquot of liquid sample can be delivered into the separation compartment (at the upstream terminus 308) from an associated sample containment means via the conduit means 340. When the manifold is arranged in the second position, the first and third manifold ports 326 and 330 are moved out of fluid communication with the separation compartment and the makeup fluid compartment such that liquid medium is no longer delivered into those compartments via conduit means 334 and 338. Further, in the second position, the second manifold port 328 is aligned to be in fluid communication with the upstream terminus 322 of the makeup fluid channel 320, and a liquid reagent, or a heated makeup fluid can be delivered into the makeup flow compartment (at the upstream terminus 322) from an associated sample containment means via the conduit means 336.

Accordingly, a liquid phase separation can be readily carried out using the apparatus 302, wherein the manifold 306 allows switching between a stand-by mode when the manifold is in the first position, and a separation mode when the manifold is in the second position. Alternatively, the above-described two position manifold can be used to alternate between a sample analysis position, corresponding to the manifold being arranged in the first position, and a sample loading position, corresponding to the manifold being arranged in the second position. The manifold 306 is switched to the second position (e.g., the position depicted in FIG. 15B) to deliver a particular volume of sample into the separation compartment. Once the sample has been delivered, the manifold is rotated clockwise about the stator to return to the first position relative the column device (e.g., the position depicted in FIG. 15C) in order to conduct liquid phase separation of the sample.

Further, as will be appreciated by those skilled in the art, movable, or multi-position manifolds, such as the manifold 306, can be coupled with any of the miniaturized column devices described herein to provide a liquid phase separation apparatus. Thus, such manifolds can be coupled to column devices which include on-device reservoirs, makeup fluid compartments, volumetric sample compartments and combinations thereof. In this manner, selective and/or temporal delivery of fluids from associated containment means into the various compartments of a miniaturized column is effected using the moveable manifolds described above.

The movable manifold can be configured in a wide variety of shapes, such as, but not limited to, an elongated finger-shaped housing or slide that is capable of either linear or rotational movement between a variety of positions, a circular or oval shaped housing capable of rotational movement between positions, or a semicircular housing that is capable of being rotated between a variety of positions. The manifold can also include any number of ports capable of communicating with an external conduit means, wherein two or more of the ports may also be capable of communicating with each other via lateral interconnecting port means. The configuration of the manifold and the layout of the ports will be generally dictated by the selected configuration of the separation compartment, the associated on-device compartments, the fluid conducting means, and the inlet ports and apertures that communicate with those elements.

A liquid phase separation apparatus may be provided having a movable manifold, wherein the manifold cooperates with an on-device volumetric sample compartment (e.g., a covered bypass channel in fluid communication with inlet and outlet means as described above), to enable the delivery of a sample plug of known volume from the sample compartment to the upstream terminus of a separation compartment. The manifold is detachably coupled to a miniaturized column device, and arranged in a first position such that external conduits disposed within two ports of the manifold enable dynamic fluid communication between the sample compartment (via the inlet and outlet means) and an associated sample containment means. A sample plug, having a volume corresponding to the dimensions of the volumetric sample compartment, is formed by the dynamic flow of sample through the compartment. By moving the manifold to a second position, different ports in the manifold are brought into fluid communication with the volumetric sample compartment inlet and outlet, whereby those ports allow the flow of an externally housed liquid medium through the sample compartment and into the separation compartment via associated conduits and/or lateral ports in the manifold. In this manner, the sample plug disposed within the volumetric sample compartment can be readily delivered to the separation compartment using known liquid injection techniques.

Figure 17:
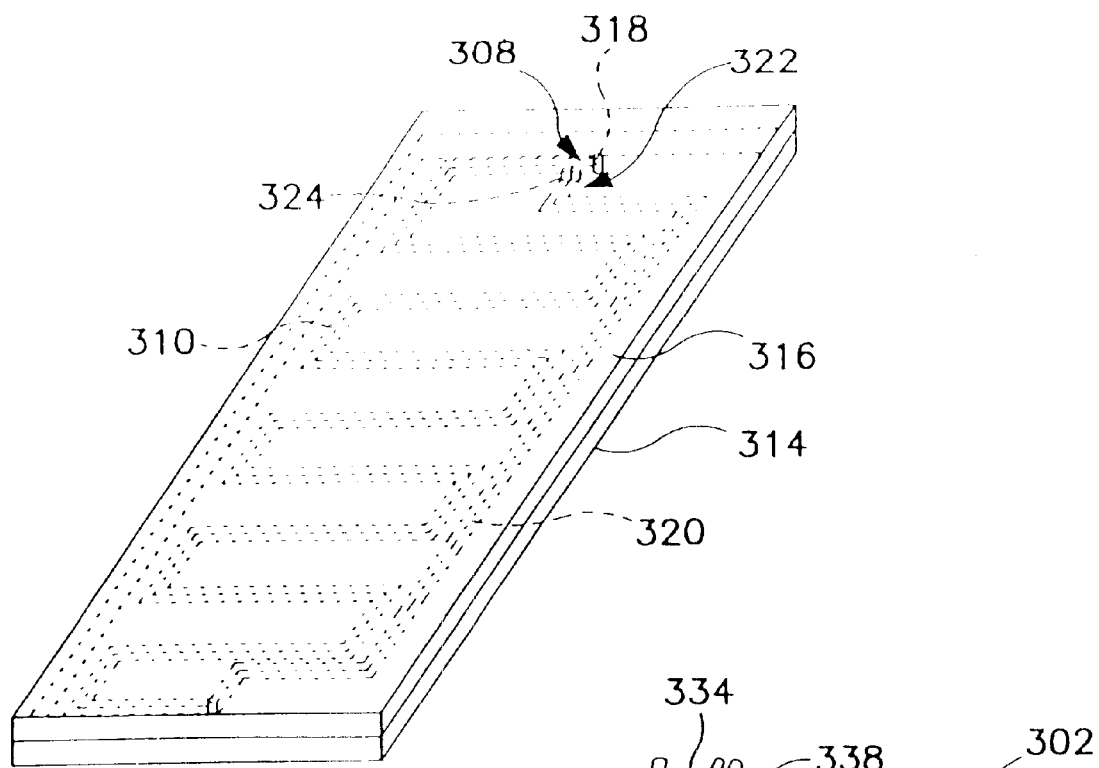
FIG. 17 is a pictorial representation of another embodiment of a miniaturized planar column device.

An apparatus may also be provided having a movable manifold that includes an internal volumetric sample compartment. Referring now to FIGS. 16 and 17, a liquid phase separation apparatus is generally indicated at 352. The apparatus includes a miniaturized column device 354, having a substrate portion 356 and a cover plate 358. A separation channel 360 is laser-ablated in a planar surface of the substrate portion 356. The separation channel has an upstream terminus 362 disposed in close proximity to three discrete laser-ablated microchannels, 364, 366, and 368, that are also formed in the substrate portion 356. The microchannel 364 has a first and second terminus, respectively indicated at 370 and 372. Likewise, the microchannel 366 has a first and second terminus, 374 and 376, and the microchannel 368 has a first and second terminus 378 and 380.

A separation compartment is formed by arranging the cover plate 358 over the planar surface of the substrate portion 356. The cover plate includes a plurality of apertures that are arranged to provide fluid communication with the separation compartment and the microchannels 364, 366 and 368 when the cover plate is in place above the substrate. Specifically, laser-ablated apertures 382 and 390, are respectively in fluid communication with the first and second terminus, 370 and 372, of the microchannel 364 to provide a first flow path. Laser-ablated apertures 384 and 392 are respectively in fluid communication with the first and second terminus, 378 and 380, of the microchannel 368 to provide a second flow path. A third flow path is provided by apertures 388 and 394, that are respectively in fluid communication with the first and second terminus, 374 and 376, of the microchannel 366. An aperture, 386, is in fluid communication with the upstream terminus 362 of the separation channel 360.

Figure 18:
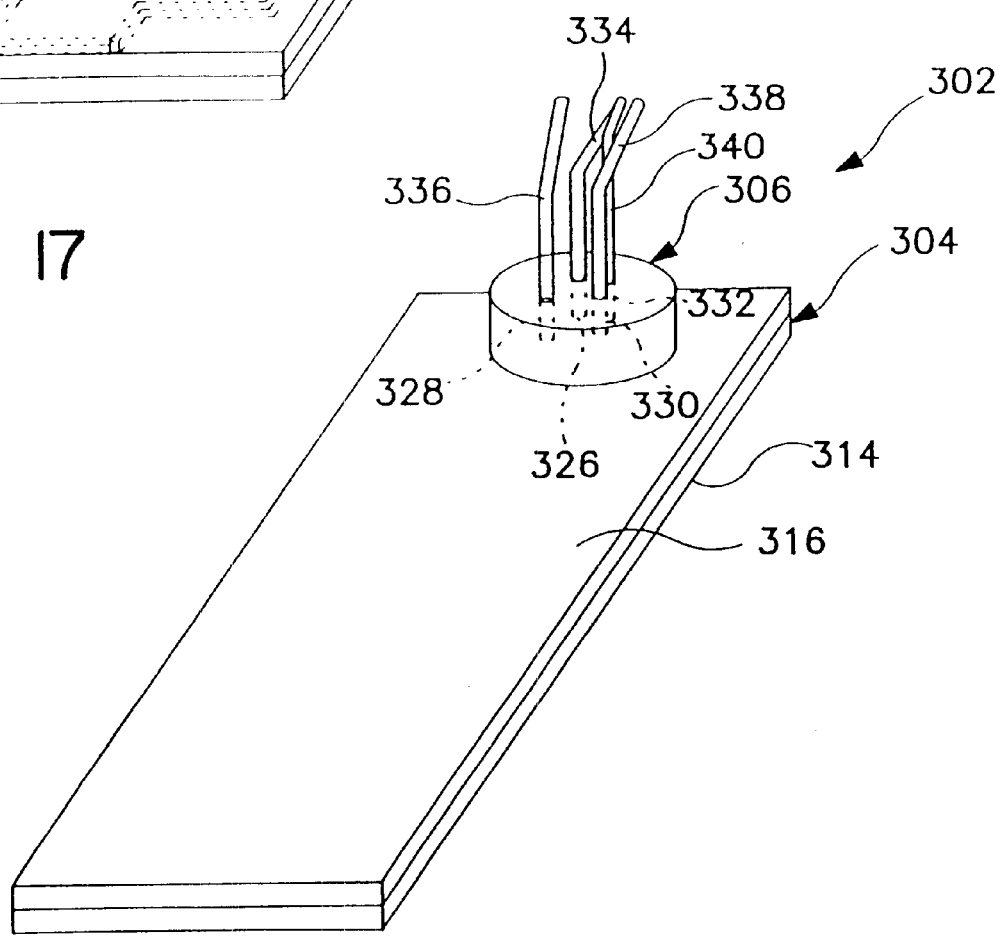
FIG. 18 is a pictorial representation of a liquid phase separation apparatus that includes the device of FIG. 17 and an externally arranged multi-position manifold means interfaced with the column device.
Figure 19A:
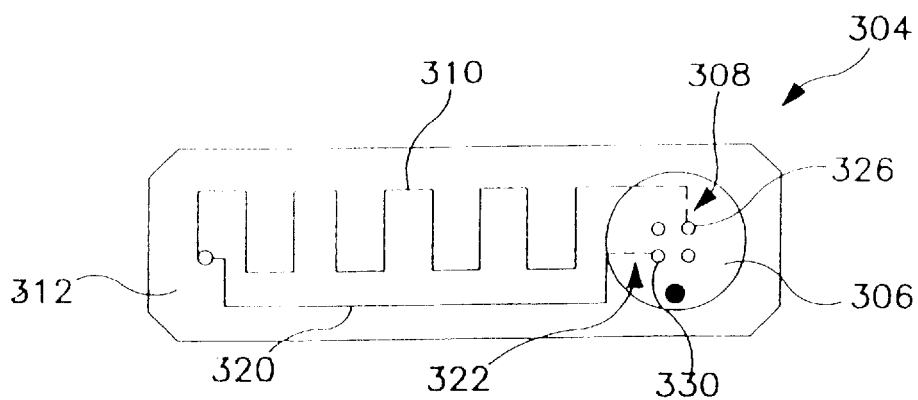
FIG. 19A is a pictorial representation of the apparatus of FIG. 18 with the manifold means arranged in a first position relative to the column device.
Figure 19B:
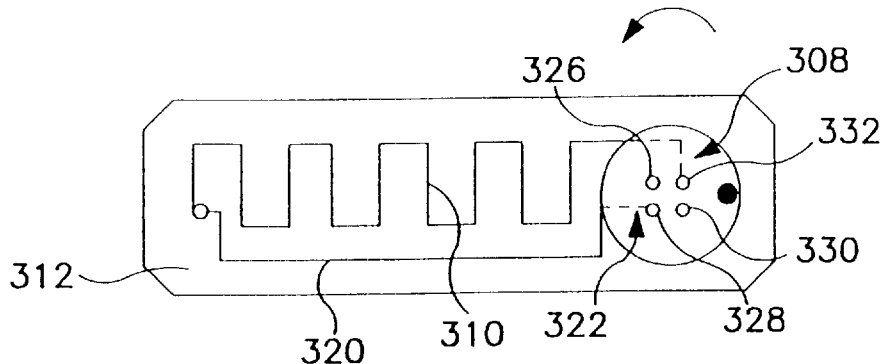
FIG. 19B is a pictorial representation of the apparatus of FIG. 18 with the manifold means arranged in a second position relative to the column device.
Figure 19C:
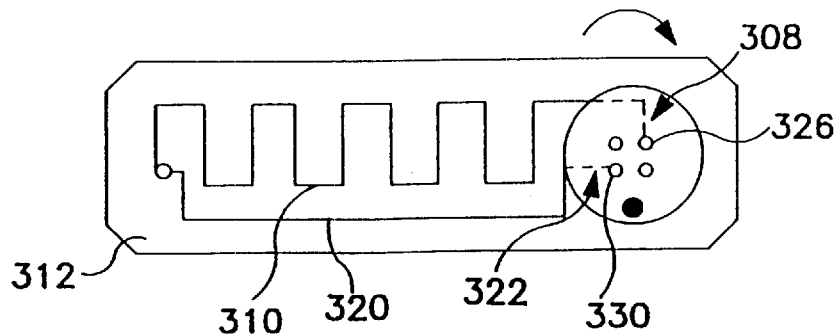
FIG. 19C is a pictorial representation of the apparatus of FIG. 18 with the manifold means returned to a first position relative to the column device.
Figure 20:
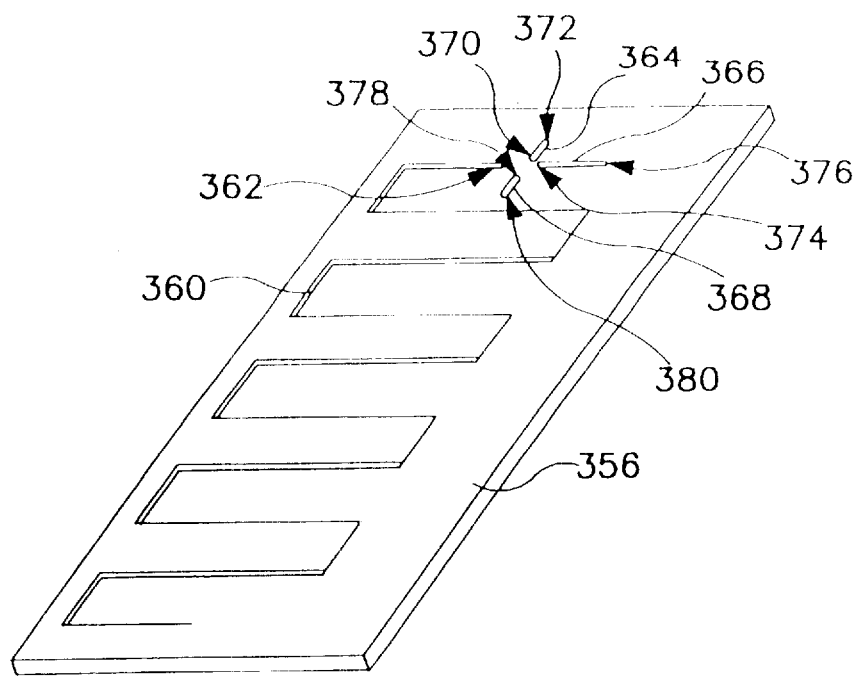
FIG. 20 is a plan view of a miniaturized column device having an alternative sample introduction means ablated in a planar substrate.
Figure 21:
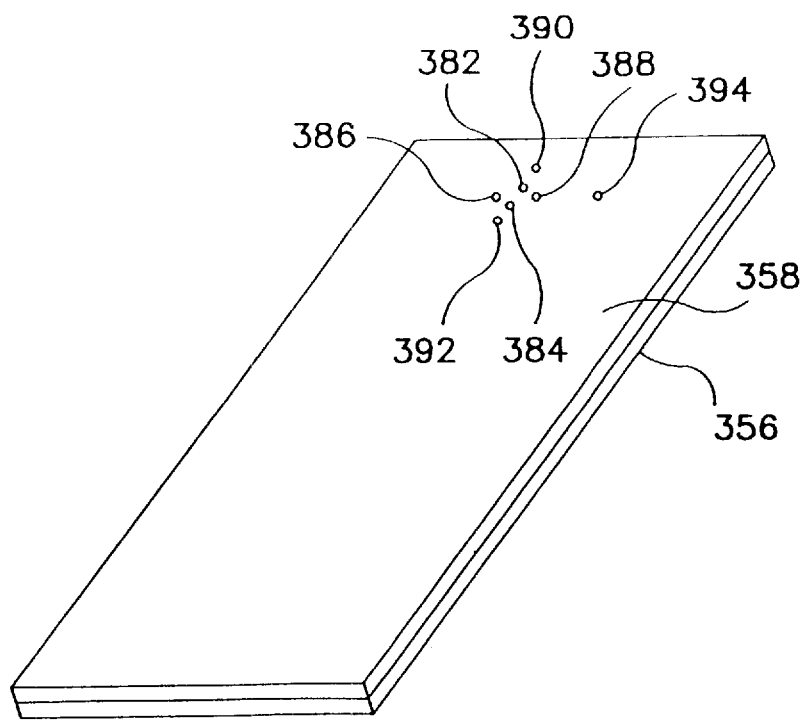
FIG. 21 is a plan view of the miniaturized column device of FIG. 20 having a cover plate aligned over the planar substrate.
Figure 22:
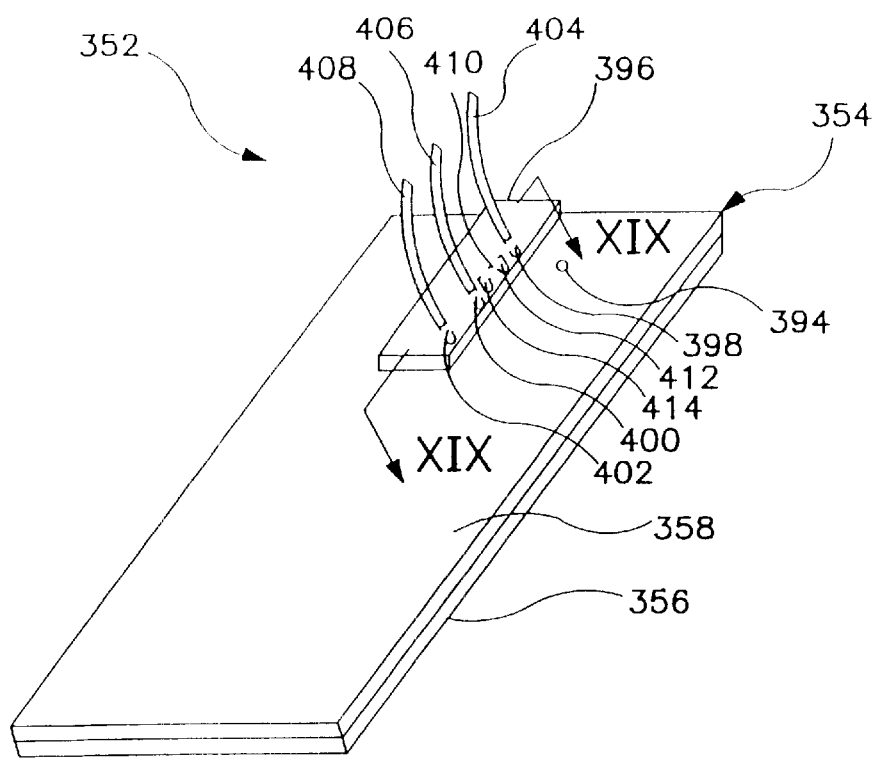
FIG. 22 is a pictorial representation of a liquid phase separation apparatus that includes the device of FIG. 21 and an externally arranged multi-position manifold means interfaced with the column device.
Figure 23:
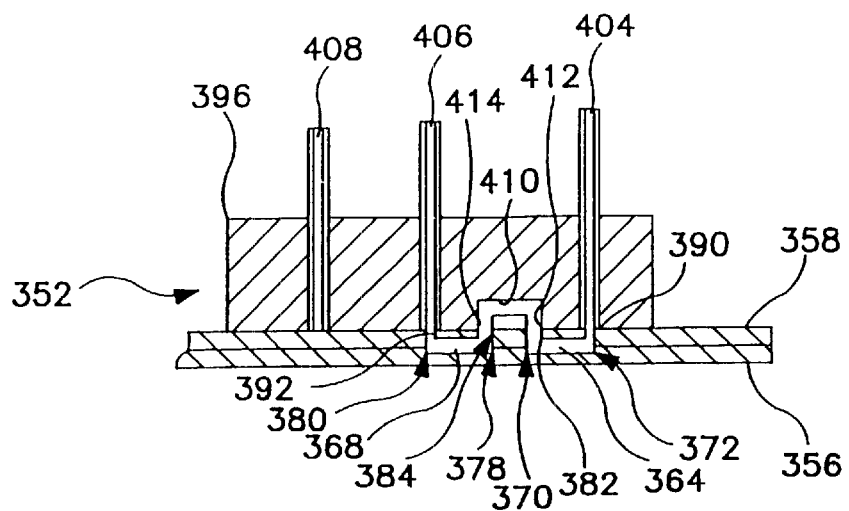
FIG. 23 is a cross-sectional view of the multi-position manifold of FIG. 22 taken along lines XIX—XIX.

Referring now to FIGS. 18 and 19, a movable manifold means 396 is coupled to the cover plate 358 to form a liquid-tight interface using known sealing techniques. Although the manifold means 396 is depicted in an elongated configuration, it is understood that the manifold can be provided in a large variety of suitable configurations as noted above. The manifold means 396 includes first, second and third ports, respectively indicated at 398, 400, and 402, wherein each port can cooperate with an external conduit means, respectively indicated at 404, 406 and 408. The manifold means 396 also includes an internal volumetric sample compartment 410, that comprises a generally U-shaped compartment having a first and second terminus, indicated at 412 and 414, respectively.

In a first position relative to the column device 354, the manifold 396 is arranged such that the manifold port 398 is in fluid communication with the aperture 390, the first terminus 412 of the internal sample compartment is in fluid communication with the aperture 382, the second terminus 414 of the internal sample compartment is in fluid communication with the aperture 384, and the manifold port 400 is in fluid communication with the aperture 392. In this first position, the manifold 396 enables one continuous flow path to be established when the conduit means 404 is communicated with an associated containment means housing a sample. Particularly, the sample is delivered to the microchannel 364 via the conduit means and passed to the volumetric sample compartment 410, continuing through the microchannel 368, and exiting the apparatus via the conduit means 406. Thus, a sample plug is formed within the volumetric sample compartment by the dynamic passage of sample therethrough.

Once a sample plug has been formed in sample compartment 410, the manifold can be moved to a second position relative to the column device 354 by rotating the manifold counter-clockwise about a pivot (not shown) to bring manifold port 402 into fluid communication with aperture 394. Further, second terminus 414 of the internal sample compartment is brought into fluid communication with aperture 388, and first terminus 412 of the internal sample compartment is brought into fluid communication with aperture 386. In this position, the sample plug can be readily flushed from the volumetric sample compartment and into the separation compartment by passing a liquid medium from an external containment means through the manifold via the conduit means 408, whereby the medium passes through the aperture 394 to flow through the microchannel 366, continuing through the sample compartment 410, and passing through the aperture 386 to the upstream terminus 362 of the separation channel 360.

One advantage the rotor has over conventional channels open to reservoirs is the possibility of switching in and out a membrane. As described above, a membrane is most often used in combination with ITP to stop the electroosmotic flow. However, one disadvantage of such use of membranes in a conventional ITP system is that the device can no longer be flushed since the membranes block the channel. The use of a rotor as described herein can overcome this problem. One rotor position can be used to insert a membrane into the fluid flow path thus preventing flow during analysis, while another rotor position can have an open connection used for to flush the sample flow compartment.

External hardware can be used to provide mechanical valving for divertable communication of various associated containment means containing, e.g., an electrolyte solution, flush solution or the liquid sample with the column device via the manifold means. Thus, a variety of injection methods can be used, including pressure injection, hydrodynamic injection or electrokinetic injection. The conduit means and any associated valving and injection means can communicate with the separation device through the manifold means, or communicate directly with the separation device by butt-coupling to apertures; however, any other suitable method of connection known in the art can be readily adapted to the invention. Further, it is noted that numerous other sample introduction and fluid interfacing designs can be practiced and still fall within the spirit of the subject invention.

Figure 24:
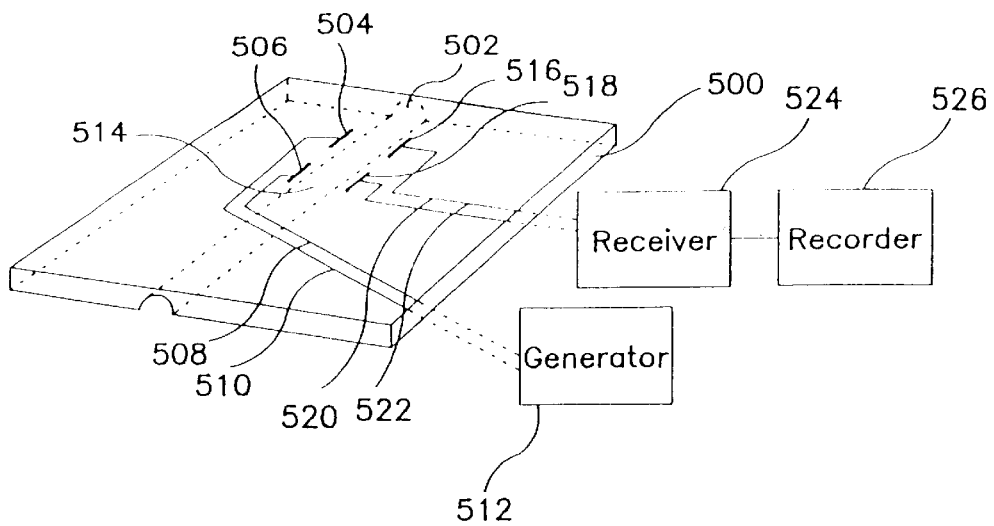
FIG. 24 is a pictorial representation and partial block diagram of one design of a planar CCD means for ion analysis of a sample in a sample processing compartment.
Figure 25:
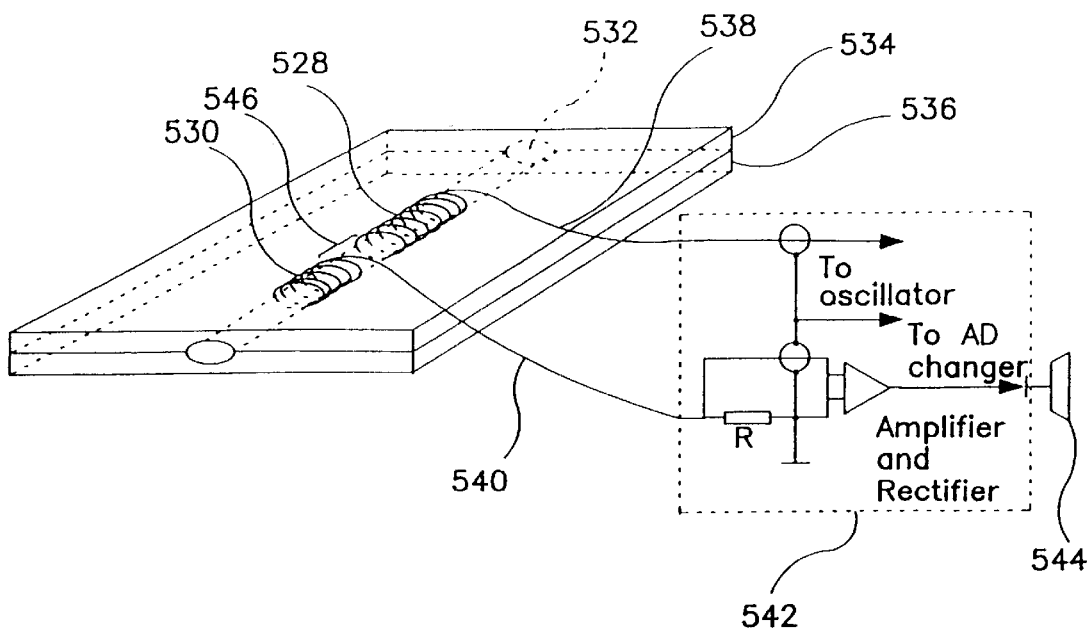
FIG. 25 is a pictorial representation and partial schematic diagram of one design of a coil CCD means for ion analysis of a sample in a sample processing compartment.

The present invention combines miniaturized device technology described above with CCD means in a single fabricated device for analysis of ionic species present in a sample. The miniaturized device includes a CCD means positioned at desired locations along a sample processing compartment. The detection means can be a planar detection means or a coil detection means fabricated directly into the separation device, as illustrated in FIG. 24 and FIG. 25, respectively, below and as disclosed in the Example which follows. Alternatively, the CCD means are formed in an insertable modular structure.

The CCD means can be formed as an integrated member of or as an attachment to the support body in any of a variety of ways that provide an electrode geometry well known in the art. Preferably, the interface area between the electrodes and the fluid is maximized. This allows for optimized signal transfer between the fluid and the detector.

Any geometry of antennae, e.g., emitting electrodes and pick-up electrodes, that allows the measurement of changes in conductivity of the sample in the sample processing compartment or sample flow channel can be used in the device. Commonly used electrode geometries, and associated circuitry, are illustrated in Gaš et al. (1980), supra, Vacík et al. (1985), supra, Zemann et al. (1998), supra, and Da Silva et al. (1998), supra. An exemplary schematic diagram of a CCD means is illustrated in FIG. 24. The basis of the detection means is a high-frequency contactless capacitive cell, formed by four electrodes applied to the surface of the substrate that opposes the surface in which the microchannel is initialed formed. Although FIG. 24 depicts a conductivity detection means in which all four electrodes are situated on the same surface of the substrate, this geometry is not intending to be limiting. For example, in a device that is made from first and second support body halves, each of which will have a first surface in which a microchannel is formed and a second surface opposing the first surface, the four electrodes may be situated in the second surface of the first support body half or one or more electrodes may be situated in the second surface of the second support body half.

Referring now to FIG. 24, support body 500 having microchannel 502 microfabricated therein is illustrated. A sample processing compartment may be formed from microchannel 502 using a cover plate, as illustrated in FIGS. 1 and 4, or using a second support body half having microfabricated therein a microchannel that is the mirror image of that in the first support body half as illustrated in FIG. 10,13 or 14. Emitting electrodes 504 and 506 are connected via traces 508 and 510 to high-frequency signal generator 512. The signal received from capacitive cell 514 is received by pick-up electrodes 516 and 518 that are, in turn, connected via traces 520 and 522 to receiver/amplifier 524, the signal from which is fed to recorder 526.

The distribution of the electromagnetic field is determined by the permittivity, permeability and conductivity of the medium. When the zones of the ionic species pass through the detector, mainly the conductivity of the medium in the detector is changed; the changes in the permittivity and permeability with dilute aqueous solutions is negligible. For a given range of measured concentration and for a given capacitive cell, the optimal frequency may be chosen so that the greatest possible changes in the signal coming to the receiver would respond to changes in the conductivity of the solution in the sample processing compartment. All traces are appropriately shielded. Optimization of the parameters of the detector is described in Gaš et al. (1980), supra, and references cited therein. A schematic diagram of the electronic components of a CCD means is provided in GAŠ et al. (1980), supra.

FIG. 25 illustrates an alternative embodiment of a CCD means based on that described in Zemann et al. (1998), supra. The capacitively coupled conductivity detector as illustrated comprises two cylindrical conducting surfaces (electrodes) 528 and 530 formed in the support bodies around microchannel 532 formed, as illustrated for the purpose of example in FIG. 25, by the opposition of mirror-image support bodies 534 and 536. The length of the electrodes can be varied from about 15 $\mu$m to about 10 mm, which will require different amplification to achieve equal signal intensities. The electrodes are connected via traces 538 and 540 to appropriate electronic circuitry 542, e.g., to an oscillator through a resistor. A voltage drop is observed which is amplified and rectified to direct current. After rectification, a direct voltage is fed in the input of an AD changer, that may be part of the data acquisition and processing system 544. However, any conventional integrator or other AD changer can be used. A detection gap 546 is constructed between the two electrodes. The length of detection gap 546 depends on the length of the microchannel and the required separation efficiency. If the detection gap is too narrow, a capacitive transfer between the electrodes can occur. Greater details of the construction and operation of a detector as illustrated in FIG. 25 can be found in Zemann et al. (1998), supra.

The electrodes can be formed directly on a nonmetalized portion of the support body. Depressions or "vias" are created in the substrate and filled with conductive material. Alternatively, the electrodes can be part of jackets used to form the final microanalysis device or additional electrode "chips" that can be attached to the external surface(s) of the device.

Referring now to FIG. 5, CCD electrodes can be provided as described herein in and/or on first transparent sheet 38. Alternatively, electrodes can be provided in and/or on first transparent sheet 38 and in or on second transparent sheet 40. In another alternative embodiment, a third sheet (not illustrated) similar to first transparent sheet 38 can be positioned in a position similar to first transparent sheet 38 but under second transparent sheet. In this embodiment, electrodes can be placed in and/or on the first and/or the second transparent sheet. First, second and/or third transparent sheets can be aligned with the support body using the apertures-and-pin means described above.

Referring now to FIG. 7A, electrodes can be provided as disclosed herein in and/or on first and second transparent sheets, indicated at 82 and 84 respectively. Referring now to FIG. 8A and FIG. 8B, electrodes can be provided as disclosed herein, for example, in and/or on first cover plate portion 88A and/or second cover plate portion 88C. Referring now to FIG. 11, electrodes can be provided as disclosed herein, for example, in and/or on the exterior surfaces of first and/or second component halves 106 and 108. Referring now to FIG. 14, electrodes can be provided as disclosed herein, for example, in and/or on the exterior surfaces of first and/or second support body halves, indicated at 154 and 156 respectively. Components in which electrodes are provided can be aligned with the support body or other components of the microanalysis device using the apertures-and-pin means described above.

An important aspect of forming the fluidic channel to be used with CCD means is to create very thin walls between the fluid in the channel and the antennae used for detection. In addition, the contact area between the electrode and the fluid in the sample flow compartment is, preferably, maximized. Although there are several ways this can be accomplished, as a person having skill in the art will readily recognize, three of which are described below for illustrative purposes.

One approach applies to the conventional methods well known in the art and described above. This typically results in a device that has the fluid channel in the center and a folded structure that covers it, as illustrated in, for example, FIG. 8 and described in the accompanying text. A drawback of this approach is that the remaining walls are fairly thick, i.e., greater than 50 $\mu$m. One way to reduce the wall thickness is to use laser ablation to make trenches in the substrate that are in close proximity to the channel and to place the electrodes in the trenches.

Alternatively, the channel can be ablated in a substrate, e.g., polyimide, that is sufficiently thin that the channel is ablated nearly through the substrate such that only a thin wall remains. The device is then covered with a cover slip, as illustrated, for example, in FIG. 1, wherein the cover slip is also a thin piece of, for example, polyimide. This provides a channel bordered by thin walls and the electrodes placed on the external surface of the substrate and the cover slip will be in close proximity to the fluid in the channel.

An additional approach involves the aforementioned procedure and, before placing the cover slip over the channel, a through hole is ablated into the substrate at the point of detection. The microfabricated substrate is now sandwiched between two cover slips, thus resulting in a device wherein the walls at the point of detection being equidistant from the channel.

In yet another approach, the electrode can be fabricated within the substrate to contact more closely the sample flow compartment.

In addition, the electrode-sample flow compartment contact area can be optimized by forming a channel having a greater width than depth relative to an electrode place above and/or below the channel.

FIG. 26 is a schematic diagram of the operation of an embodiment of a miniaturized ion analysis system using a CCD means for ion analysis of a sample in a sample processing compartment using isotachophoresis. It must be emphasized that the configuration illustrated in FIG. 26 is for illustrative purposes only and is not intended to be limiting in any manner. One of skill in the art will recognize that the placement of the buffer reservoirs and/or CCD means can vary depending on the particular application for which the device is to be used.

Referring now to FIGS. 26A–F, the device, generally indicated at 600, comprises sample flow compartment 602 having first 604 and second 606 termini. First terminus 604 is in fluid communication with reservoir 608 containing a source of terminating electrolyte. It will be recognized that, although an on-device reservoir is illustrated in FIG. 26, first terminus 604 may be connected to an off-device source of terminating electrolyte. Second terminus 606 is in fluid communication with reservoir 610 which may serve as a source of leading electrolyte or as a waste reservoir; in the embodiment illustrated in FIG. 26, reservoir 610 serves as a leading electrolyte source reservoir. Again, terminus 606, optionally, can be interconnected with an external reservoir. Sample flow compartment 602 is also in fluid communication with reservoirs 612, 614 and 616 via sample flow compartments 618, 620 and 622. In the embodiment illustrated in FIG. 26, reservoir 612 serves as a waste receptacle, reservoir 614 serves as a source of sample and 610 serves as a source of leading electrolyte. As above, sample flow compartment 602, optionally, can be interconnected via sample flow compartments 618, 620 and 622, or by an alternate means, to off-device reservoirs that serve the purpose of reservoirs 612, 614 and 616. The embodiment of the invention illustrated in FIG. 26 includes CCD means 624 and 626 situated for detecting ionic species present in sample flow compartment 602. In particular, conductivity detection means 624 is situated upstream from the point at which leading electrolyte can be introduced into the compartment, i.e., upstream of the interconnection between sample flow compartment 602 and sample flow compartment 622. Conductivity detection means 626 is situated just upstream of terminus 606. In the embodiment illustrated in FIG. 26, the flow of fluids out of or into reservoirs 608 through 606 can be controlled by appropriate on-device mechanical valving means. Furthermore, reservoirs 608, 610 and 616 are connected to sources by which current is applied to the fluid in sample flow compartment 602 as desired.

In operation of the embodiment of the invention illustrated in FIG. 26, the order of the steps of this operation being clearly variable, the downstream portion of sample flow compartment 602 is flushed with leading electrolyte by introducing the leading electrolyte from reservoir 610 through sample flow compartment 602 into waste reservoir 608 (FIG. 26A). The upstream portion of sample flow compartment 602 is flushed with terminating electrolyte by introducing the terminating electrolyte from reservoir 608 through sample flow compartment 602 into waste reservoir 612 (FIG. 26B). A sample "plug" is then introduced into sample flow compartment 602 to be in fluid and ionic contact with the terminating buffer by introducing the sample from reservoir 614 into waste reservoir 612 through sample flow compartments 618 and 620 (FIG. 26C). Finally, the leading electrolyte is introduced into sample flow compartment 602 to be in fluidic and ionic contact with the sample plug by introducing the electrolyte from reservoir 610 to waste reservoir 612 through sample flow compartments 602 and 618.

Optional preseparation step, preconcentration step and sample identification step can be included preceding the final analytical separation step. With respect to the desirability of performing a preseparation step, for example, if a sample is known to be composed of the ionic analyte of interest in a low quantity relative to another ionic species, a large volume injection of sample can be made using a device having a large-volume capacity preseparation flow compartment as part of sample flow compartment 602. Current can then be applied to stack the ionic species within the sample in the large-volume capacity preseparation flow compartment and the high quantity component detected and identified at CCD means 624 situated immediately downstream of the large-volume capacity preseparation flow compartment and dumped to reservoir 616 as illustrated in FIG. 26E and FIG. 26F. After switching the ground point to reservoir 610 the portion of the sample slug remaining after the major component is dumped to waste is subject to analytical separation, detection, quantitation and identification based on conductivity using CCD means 626 as illustrated in FIG. 26F.

For example, it may be desirable to analyze the ionic acids present in orange juice. However, the quantity of citrate in orange juice is sufficiently large to overwhelm the ability of the system to detect more minor components in the orange juice. Thus, in a series of pretreatment steps, the ionic species in the orange juice can be stacked and, by passing the prestacked ionic species past a first CCD means, identified. Thereafter, the citrate component of the orange juice can be dumped to waste. The remaining components are then subject to the analytical separation, identification and quantitation steps by changing the ground point as described above, restacking the remaining species and passing the stack past a second CCD means.

In the above described embodiment, the device is used in a process comprising at least two stages, a preanalysis/sample processing stage that can include preseparation, preconcentration and/or sample identification and an analytical stage in which the analyte of interest in the sample is detected, identified and quantified. Both of these stages have been described as isotachophoresis processes. In an alternative embodiment, as illustrated in FIGS. 27A–F, the device, generally indicated at 700 can be used in a mode wherein the analytical stage is run in, for example, a capillary zone electrophoresis mode. Thus, the initial steps of operation include flushing sample flow compartment 702 with terminating electrolyte as illustrated in FIG. 27A (from reservoir 710 to waste reservoir 712) and FIG. 27B (from reservoir 708 to waste reservoir 712), introducing a sample "plug" as illustrated in FIG. 27C (from sample reservoir 714 to waste reservoir 712) and flushing the system with leading electrolyte as illustrated in FIG. 27D (from reservoir 716 to waste reservoir 712), the ionic species are stacked and separated as illustrated FIG. 27E. Finally, analytical separation is achieved in a capillary zonal electrophoresis mode in which the leading and terminating electrolytes that are in liquid and ionic contact with the final sample plug are the same. The principals of zonal electrophoresis, in general, and capillary zonal electrophoresis, in particular, and guidance for the design of such analytical methods can be found in Landers et al. "Handbook of Capillary Electrophoresis" (CRC Press, 2d Edition).

Figure 28:
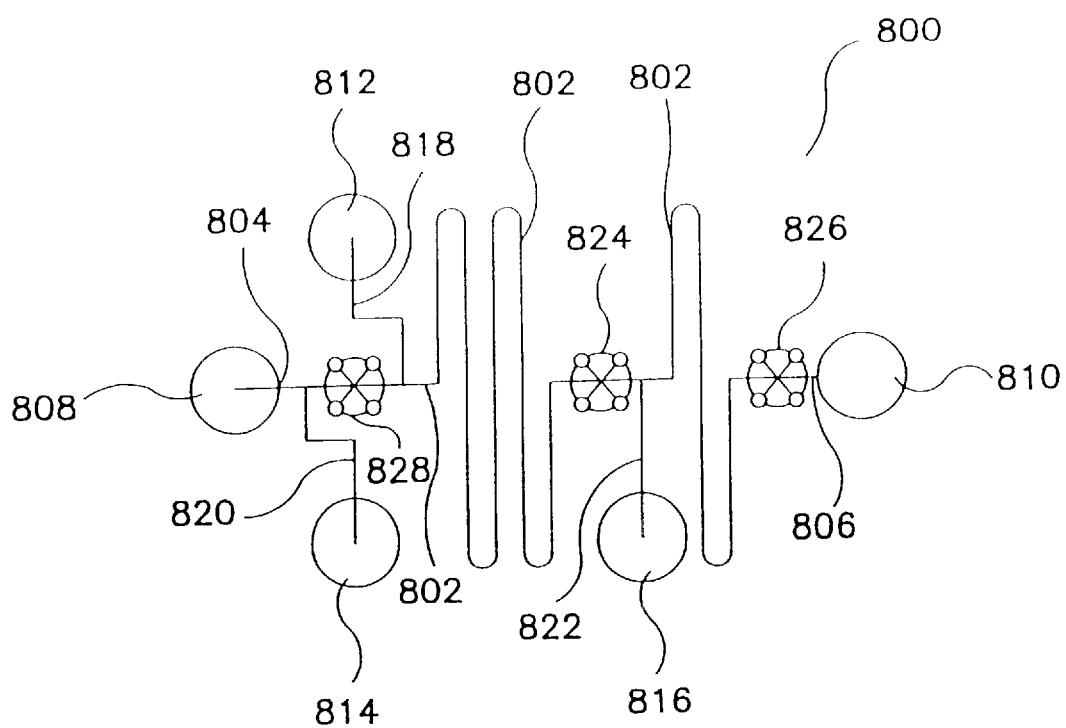
FIG. 28 is a schematic diagram of a miniaturized ion analysis system using a CCD means for ion analysis of a sample in a sample processing compartment. In this embodiment, a CCD means is situated near the point at which the sample plug is introduced into the sample flow compartment.

Another alternate embodiment of the device disclosed and claimed herein is illustrated in FIG. 28. In this embodiment, the device, generally indicated at 800, comprises sample flow compartment 802 having first 804 and second 806 termini. First terminus 804 is in fluid communication with reservoir 808 containing a source of terminating electrolyte. It will be recognized that, although an on-device reservoir is illustrated in FIG. 28, first terminus 804 may be connected to an off-device source of terminating electrolyte; in the embodiment illustrated in FIG. 28, reservoir 610 serves as a leading electrolyte source reservoir. Second terminus 806 is in fluid communication with reservoir 810 which may serve as a source of leading electrolyte or as a waste reservoir. Again, terminus 806, optionally, can be interconnected with an external reservoir. Sample flow compartment 802 is also in fluid communication with reservoirs 812, 814 and 816 via sample flow compartments 818, 820 and 822. In the embodiment illustrated in FIG. 28, reservoir 812 serves as a waste receptacle, reservoir 814 serves as a source of sample and 810 serves as a source of leading electrolyte. As above, sample flow compartment 802, optionally, can be interconnected via sample flow compartments 818, 820 and 822, or by an alternate means, to off-device reservoirs that serve the purpose of reservoirs 812, 814 and 816. The embodiment of the invention illustrated in FIG. 28 includes CCD means 824, 826 and 828 are situated for detecting ionic species present in sample flow compartment 802. In particular, conductivity detection means 828 is situated near the point at which the sample plug is introduced into the sample flow compartment. The method of using this particular embodiment comprises flushing the sample through the detection means before analytical separation to determine the conductivity of the sample. Thus, if desired prior to analytical separation, detection, quantitation and identification, the sample can be diluted or the conductivity otherwise adjusted to be within the range of conductivity optimal for analytical separation. An additional reservoir containing a source of diluent interconnected by an accessory sample flow compartment with the main sample flow compartment can be microfabricated in the substrate as needed. In an alternate embodiment, a plurality of CCD means can be situated along the sample flow compartment to image the state of the separation as it progresses. Such an approach can be used to determine whether separation is complete, to obtain physical parameters such as mobility of the ions in the sample for identification thereof, or to measure EOF.

In another alternate embodiment, the device can be configured to allow optimization of the ion analysis for an analyte present in a lower or in the least quantity in the sample. In ITP, stacking between the leading and terminating electrolytes of ionic species in a sample results in distinct bands each of which has a different and characteristic conductivities. The length of the band for a given species, i.e., the duration of time required for the leading edge and trailing edge of a band to pass the detection means, depends not on the concentration of ionic species in that band but rather on the quantity of ionic species therein. Thus, for example, a species present in a relatively low quantity in the sample would provide a relatively narrow band. Tapering the sample flow compartment to a more narrow bore at the point of detection results in lengthening the duration of time for the bands to pass through the detection means. thereby enhancing the sensitivity for detection of species present in relatively small amounts. A tapered sample flow compartment can also be used to introduce a larger volume of sample that would form bands that get increasingly longer as the compartment becomes more narrow.

As disclosed above, a CCD means can be situated at the point of injection to provide information about the conductivity of an unknown before analysis, e.g., to aid in selection of leading and trailing buffers or to allow dilution of the sample to correct conductivity for analysis on the particular device in use. In addition, a CCD means can be situated at or near the point at which the terminating electrolyte is introduced into the sample flow compartment to allow for correction of electroosmotic flow ("EOF") correction by adding counter-flow.

Isotachophoresis has typically been carried out in commercially available or laboratory-made ITP instruments, generally in closed systems. However, several instruments than can be used for ITP employ open capillaries and, in these systems, an electroosmotic flow will act on the ITP system and four modes can be distinguished, namely the cationic mode, the anionic mode, the reversed cationic mode and the reversed anionic mode. The applicability of these modes depends on the velocity of the EOF. The velocity of the EOF varies with the choice of leading and terminating electrolyte and the composition of the sample. Due to the variation in the velocity of the EOF, the reproducibility in quantitative analysis can be a problem. Hence, an internal standard is often used to correct for undesirable fluctuations in the EOF. Attempts to suppress EOF include closing the system by placing a membrane at the inlet and outlet sides or including an additive, such as methylhydroxyethylcellulose. The present invention affords an alternative means by which EOF can be quantitated and successfully suppressed. This embodiment of the invention is best understood by reference to the following discussion.

As mentioned above, four different ITP modes can be distinguished. These four modes are illustrated in FIGS. 29A–D. FIG. 29A illustrates the cationic ITP mode in which the sample flow compartment 900 is filled with leading electrolyte 902 at the cathode 912, while the terminator electrolyte 904 is present on the inlet (anode 914) side of the apparatus. The sample solution 906 is introduced between 902 and 904 and, in operation, will be separated into stack elements that correspond to analytes 906A, 906B and 906C. In typical installations, detector 1000 is placed at the outlet side. As depicted by arrows 908 and 910 above the sample flow compartment, the EOF (910) will generally act in the direction from anode to cathode through which the cationic ITP system (908) will be pushed forward with an extra velocity of the EOF compared with ITP in closed system.

In FIG. 29B the situation is depicted for the anionic ITP mode. The cathode 934 is placed at the inlet side and the anode 932 at the outlet side. The sample flow compartment 920 is filled with the leading electrolyte 922 and the terminating electrolyte 924 is present at the inlet side. As depicted by arrows 928 and 930 above the sample flow compartment, the EOF (930) will generally act in the direction from anode to cathode through which the anionic cationic ITP system (928) will be inhibited from moving forward. This set up can be compared with ITP with counterflow and is generally useful only if the velocity of the leading ions is larger than that of the EOF during the analysis. In this configuration, anionic species with mobilities smaller than that of the EOF must also migrate to the anode according to the ITP condition.

If the velocity of the EOF is greater than that of the anionic ITP system, there would be a net migration into the direction of the cathode. The only way to configure the system in this situation is to place the anode at the inlet side and the cathode at the outlet side, as depicted in FIG. 29D. The sample flow compartment 960 is filled with leading electrolyte 962 at the anode 974, while the terminator electrolyte 964 is present on the outlet (cathode 972) side of the apparatus. The sample solution 966 is introduced between 962 and 964 and, in operation, will be separated into stack elements that correspond to analytes 966A, 966B and 966C. Although the ITP separation takes place in the direction of the anode (968), there would be a net velocity of the ITP system in the direction of the cathode (972, detector side) and the components will be detected in a reversed order compared with a normal anionic ITP system, i.e., first the terminating electrolyte, than all sample components with increasing mobilities and finally the leading ions. This is called "reverse anionic ITP mode." If the velocity of the leading ions is greater than that of the EOF 970, the ITP system will move to the anode and the components cannot be detected at the outlet.

Analogous to the reverse anionic mode is the reverse cationic mode that can be applied if there is a reversed EOF 950 from cathode 954 to anode 952 with a velocity greater than that of the cationic ITP system (see FIG. 29C). Here the cathode must be placed at the inlet and the anode at the outlet. The sample flow compartment 940 is filled with the terminating electrolyte 944 and the inlet vessel with the leading electrolyte 942. As with reverse anionic mode, the components 966A, 966B, and 966C are detected in the reversed order.

The velocity of the EOF is extremely important in the migration behavior of the ITP systems. In order to counter the effect of EOF on ITP flow a membrane could be integrated into the microstructure. Alternatively, the viscosity of the electrolyte solutions can be increased. However, the flexibility of a miniaturized ITP device comprising CCD means as disclosed herein allows a preferred method by which EOF can be detected and, if desired, e.g., when ITP migration and EOF are counter to one another, corrected by application of a force equal and opposite to that of the EOF.

ITP is run in a constant current mode. Thus, the field strength in the electrolytes and in each band in the stack will be different. Since EOF is related to field strength there will be different regions of osmotic flow in each component within the sample flow compartment. The concentration of ions in the terminating electrolyte solution, as it enters the sample flow compartment, will undergo an adaptation such that the number of ions/unit volume changes to allow the terminating electrolyte to carry the current. Accordingly, a boundary will develop between the terminating electrolyte that has so adapted and the terminating electrolyte in the reservoir and in the sample flow compartment that has not yet undergone such adaptation. The EOF will cause the boundary to move down the sample flow compartment.

The difference in conductivity of the electrolyte on either side of the boundary can be detected by placing a CCD means at the point of entrance of the terminating electrolyte. Application of a counterbore sufficient to counteract the EOF can be determined by monitoring the location of the boundary until it has been found to stay fixed. The counterbore can be applied, for example, by use of a downstream on- or off-device fluid reservoir containing sufficient fluid to counter the EOF for the duration of the ITP analysis.

In addition to the CCD means, other detection means may be interfaced with sample separation compartment, e.g., to serve as a sample detector and conductivity detection means trigger. For this purpose, an aperture is formed for communication with the elongate bore or sample processing compartment formed in the support body at a point upstream of the conductivity detection means. A second aperture may be formed to communicate with the elongate bore or sample processing compartment downstream of the CCD means. The apertures serve as conduits for placing lightguide means, electrodes or other detection means in communication with the elongate bore or sample processing compartment to detect a sample passing therethrough. For example, first and second lightguide means (not shown) can be interfaced with first and second apertures to communicate with the sample processing compartment. Such lightguides can comprise optical fibers that are capable of sample illumination and light collection to enable near IR or UV-VIS optical detection of separated analytes passing through the separation compartment. The detection of separated analytes prior to their entry into the CCD means can be used for conductivity signal enhancement.

The choice of leading and terminating electrolytes is critical to the successful ion analysis by isotachophoresis. The mobilities of the leading electrolytes and terminating electrolytes must bracket the mobilities of the species in the sample. The ion analysis device disclosed and claimed herein can designed in a number of configurations to ensure that the leading and terminating electrolytes can be used with the sample of interest. As indicated above, a CCD means can be situated on the device in a location relative to the point of injection of a sample so that the conductivity of the sample can be determined prior to analysis. If necessary, the sample can then be diluted to adjust the conductivity for analysis. Optionally, the sample can then be subject to a preseparation step to allow shunting to waste portions of the sample that are not required for subsequent analytical separation.

The ability to place the CCD means, thereby allowing determination of the conductivity of a sample, and subsequently to adjust the conductivity of the sample prior to analytic separation, allows the device to have multiple reservoirs placed thereon with prepackaged leading and terminating electrolytes contained therein. This not only affords additional flexibility in terms of the type of sample that can be analyzed but also allows the end-user to use the device without any a priori knowledge of the conductivity of the sample and without any foreknowledge of how to select appropriate leading and terminating electrolytes. A catalog of devices can be prepared having a variety of prepackaged leading and terminating electrolytes.

The advantages of having a miniaturized ion analysis device as disclosed and claimed herein: (1) ease of use in that the user does not have to select the appropriate leading and trailing buffers which can be prepackaged on each chip; (2) integrated CCD means provides for a system that is easier to use that a tube-based system; (3) the CCD means avoid problems associated with systems in which the electrodes contact the sample; (4) geometry flexibility allows for a preseparation step, analyte selection and/or a final separation step on some or all of the analytes; (5) increased sensitivity of ITP analysis; and (5) the microstructure can be optimized for the smallest sample; and (6) low cost-high volume manufacture of consumable devices.

It is to be understood that while the invention has been described in conjunction with the preferred specific embodiments thereof, that the description above as well as the examples which follow are intended to illustrate and not limit the scope of the invention. Other aspects, advantages and modifications within the scope of the invention will be apparent to those skilled in the art to which the invention pertains.

We claim:

1. A method for analyzing ionic species present in a sample, comprised of:
   (a) providing a miniaturized ion analysis system for sample preparation and analysis comprising;
      a microfabricated support body having first and second substantially planar opposing surfaces wherein the support body has a microchannel microfabricated in the first planar surface, a cover plate arranged over the first planar surface, wherein the cover plate in combination with the microchannel forms a sample flow compartment, an inlet port and an outlet port communicating with the sample flow compartment, wherein the inlet and outlet ports enable passage of fluid from an external source through the sample flow compartment, and a contactless conductivity detection ("CCD") means in electrical communication with the sample flow compartment such that the detection means is capable of detecting the presence in the sample flow compartment of a fluid containing a detectable ionic species;

(b) flushing the sample flow compartment with a leading electrolyte;

(c) introducing a sample into the sample flow compartment such that the sample is in fluidic and ionic communication with the leading electrolyte;

(d) introducing a terminating electrolyte into the sample flow compartment such that the sample is in fluidic and ionic communication with the terminating electrolyte;

(e) stacking the ionic species present in the sample by applying a current across the leading and terminating electrolytes to provide stacked ionic species;

(f) preseparating the stacked ionic species; and (g) detecting the presence in the sample flow compartment of the pre-separated stacked ionic species.

2. The method of step 1, further comprising flushing the sample through the sample flow compartment to determine the conductivity of the sample before step (e).

3. The method of step 1, further comprising situating a CCD means over the inlet port, and, concurrently with step (e) applying a counterbore sufficient to counteract an electroosmotic flow.

4. A method for analyzing ionic species present in a sample, comprising:

(a) providing a miniaturized ion analysis system for sample preparation and analysis comprising, a microfabricated support body having first and second component halves each having substantially planar opposing interior and exterior surfaces, a first microchannel microfabricated in the interior surface of the first support body half and a second microchannel microfabricated in the interior surface of the second support body half, wherein each of the microchannels is so arranged as to provide the mirror image of the other, an elongate bore formed by aligning the interior surfaces of the support body halves in facing abutment with each other whereby the microhchannels define a sample flow compartment, an inlet port and an outlet port communicating with the sample flow compartment, wherein the inlet and outlet ports enable passage of fluid from an external source through the sample flow compartment, and a contactless conductivity detection ("CCD") means in electrical communication with the sample flow compartment such that the detection means is capable of detecting the presence in the sample flow compartment of a fluid containing a detectable ionic species;

(b) flushing the sample flow compartment with a leading electrolyte;

(c) introducing a sample into the sample flow compartment such that the sample is in fluidic and ionic communication with the leading electrolyte;

(d) introducing a terminating electrolyte into the sample flow compartment such that the sample is in fluidic and ionic communication with the terminating electrolyte;

(e) stacking the ionic species present in the sample by applying a current across the leading and terminating electrolytes to provide stacked ionic species;

(f) preseparating the stacked ionic species; and (g) detecting the presence in the sample flow compartment of the stacked ionic species.

5. The method of step 4, further comprising flushing the sample through the sample flow compartment to determine the conductivity of the sample before step (e).

6. The method of claim 4, further comprising situating a CCD means over the inlet port, and, concurrently with step (e) applying a counterbore sufficient to counteract an electroosmotic flow.

* * * * *